US012582409B2

(12) United States Patent
Bergner et al.

(10) Patent No.: US 12,582,409 B2
(45) Date of Patent: Mar. 24, 2026

(54) DEVICES AND METHODS FOR BLOOD FLOW REGULATION

(71) Applicant: Laminate Medical Technologies Ltd., Tel Aviv (IL)

(72) Inventors: Yair Bergner, Tel Aviv (IL); Tamar Gilon, Tel Aviv (IL)

(73) Assignee: LAMINATE MEDICAL TECHNOLOGIES LTD., Tel Aviv (IL)

( * ) Notice: Subject to any disclaimer, the term of this patent is extended or adjusted under 35 U.S.C. 154(b) by 414 days.

(21) Appl. No.: 18/246,308

(22) PCT Filed: Sep. 28, 2021

(86) PCT No.: PCT/IB2021/058856
§ 371 (c)(1),
(2) Date: Mar. 22, 2023

(87) PCT Pub. No.: WO2022/064471
PCT Pub. Date: Mar. 31, 2022

(65) Prior Publication Data
US 2023/0371958 A1     Nov. 23, 2023

Related U.S. Application Data

(60) Provisional application No. 63/084,152, filed on Sep. 28, 2020.

(51) Int. Cl.
| | |
|---|---|
| *A61B 17/135* | (2006.01) |
| *A61B 17/00* | (2006.01) |
| *A61M 1/36* | (2006.01) |

(52) U.S. Cl.
CPC ... *A61B 17/1355* (2013.01); *A61M 1/362262* (2022.05); *A61M 1/3655* (2013.01); *A61B 2017/00778* (2013.01)

(58) Field of Classification Search
CPC ......... A61M 1/3655; A61M 2205/3334; A61F 2/06; A61F 2/04; A61F 2002/068;
(Continued)

(56) References Cited

U.S. PATENT DOCUMENTS

| | | | |
|---|---|---|---|
| 5,370,899 A | 12/1994 | Conway et al. | |
| 2009/0156978 A1 | 6/2009 | Faul et al. | |

(Continued)

FOREIGN PATENT DOCUMENTS

| | | |
|---|---|---|
| CN | 103845768 A | 6/2014 |
| JP | 4675560 B2 | 4/2011 |

(Continued)

OTHER PUBLICATIONS

International Search Report mailed Jan. 19, 2022 for International Patent Application No. PCT/IB2021/058856 (3 pages).
(Continued)

*Primary Examiner* — Nicholas J. Weiss
*Assistant Examiner* — Seth Han
(74) *Attorney, Agent, or Firm* — Smith, Gambrell & Russell, LLP.

(57) ABSTRACT

A vascular constricting device for constricting vascular lumens to regulate blood flow in a vascular system includes a cuff having an inflatable body and a frame adapted for wrapping round a vascular lumen, such as a native blood vessel or non-native graft, and a pump having an internal reservoir for doling a fluid and a fluid circuit for controlling the flow of fluid between the reservoir and the inflatable body for selectively inflating and deflating the inflatable body. In a hemodialysis treatment, the vascular constricting device is actuated to inflate the inflatable body to restrict blood flow and lower blood flow rate during off-treatment periods, and is actuated to deflate the inflatable body to permit an unrestricted blood flow and a higher blood flow rate during on-treatment periods.

64 Claims, 25 Drawing Sheets

(58) Field of Classification Search
     CPC .................. A61F 2/07; A61F 2002/072; A61F
                          2002/075; A61F 2002/077; A61F
                                                    2250/001
     See application file for complete search history.

(56)                    References Cited

U.S. PATENT DOCUMENTS

| | | |
|---|---|---|
| 2011/0202079 A1 | 8/2011 | Schoenle et al. |
| 2016/0022459 A1 | 1/2016 | Price et al. |
| 2018/0050180 A1 | 2/2018 | Bacino et al. |
| 2018/0177486 A1 | 6/2018 | Gifford, III et al. |
| 2019/0083228 A1 * | 3/2019 | Dickinson .......... A61B 17/3468 |
| 2019/0133745 A1 | 5/2019 | Janardhan et al. |
| 2019/0231511 A1 * | 8/2019 | Winner ................... D03D 1/00 |

FOREIGN PATENT DOCUMENTS

| | | | | |
|---|---|---|---|---|
| WO | WO-2020165712 A1 * | 8/2020 | ........... | A61B 8/0833 |
| WO | WO-2021018367 A1 * | 2/2021 | ....... | A61B 17/12013 |

OTHER PUBLICATIONS

International Search Report and Written Opinion of the International Searching Authority mailed Jan. 19, 2022 for International Patent Application No. PCT/IB2021/058856 (9 pages).

* cited by examiner

Artery    Vein

Blood from
dialysis machine

Blood to
dialysis machine

Vein

Fistula

Artery

Artery

Vein

Graft

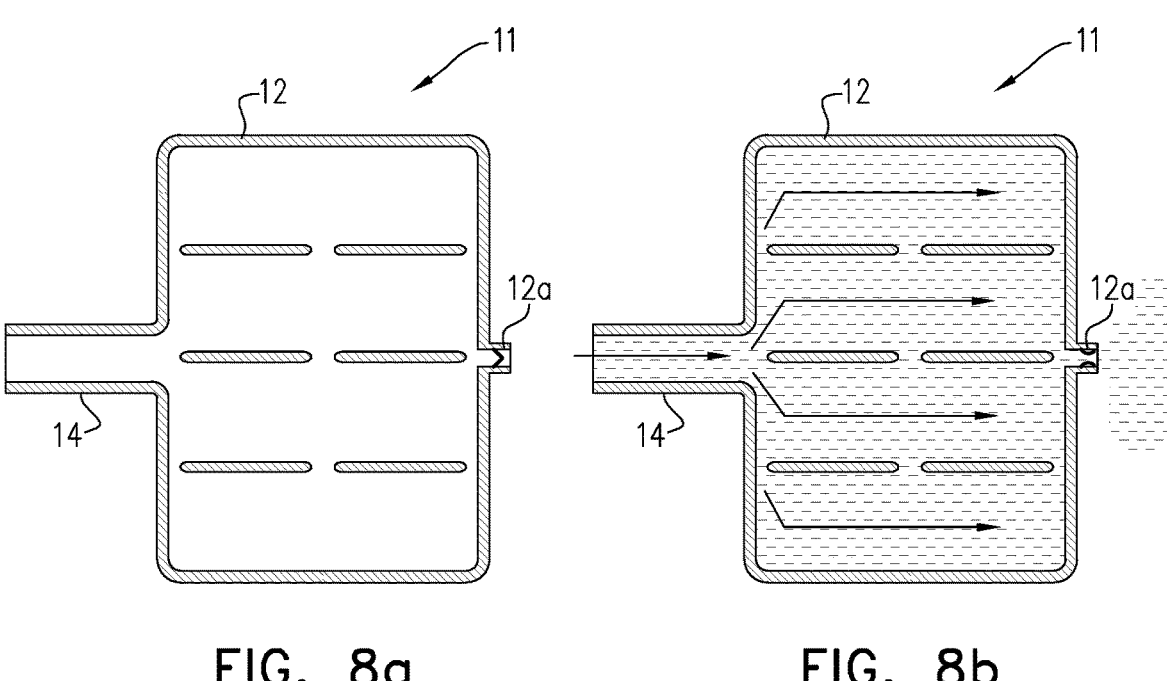
FIG. 8a
FIG. 8b
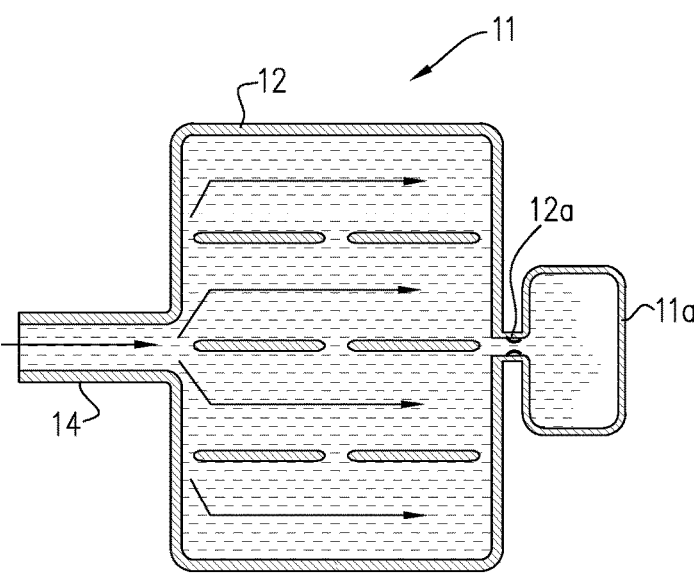
FIG. 8c

OFF POSITION

ON POSITION

ON-OFF

30

30a

30a

30a

DEVICES AND METHODS FOR BLOOD FLOW REGULATION

FIELD OF THE INVENTION

The present invention relates to devices and methods for controlling blood flow through blood vessels in a region of an arteriovenous junction, particularly in connection with hemodialysis.

BACKGROUND OF THE INVENTION

Patients with end-stage renal disease regularly undergo hemodialysis to remove toxins, waste, salt, and extra water from the body and prevent them from building up. Hemodialysis is a treatment for kidney failure that uses an extracorporeal machine to send the patient's blood through a filter, called a dialyzer. The blood is withdrawn from the distal part of a surgically created vascular access, purified, and then returns to its proximal part towards the heart, as shown in FIG. 1.

In modern practice, extraction of blood flow with a suitable flow rate within the target range for processing in a dialysis machine is achieved through the use of an arteriovenous junction (AV junction, or AVJ), whereby a blood flow from an artery is diverted from its normal path and redirected to a vein. The two most common forms of AV junctions for long-term vascular access in dialysis are a native arteriovenous fistula (AV fistula, or AVF) and an arteriovenous graft (AV graft, or AVG), as illustrated in respective FIGS. 2a and 2b. Based on the Kidney Disease Outcomes Quality Initiative (KDOQI) guidelines, the blood flow rate threshold for hemodialysis through an AVF is above 500 ml/min and 600 ml/min for AVG.

In an AVF method, as seen in FIG. 2a, openings are created in both an artery and vein and the borders of these separate openings are then attached to form an anastomosis such that the vein is joined to the artery to provide a common passageway, conventionally referred to as a fistula, through which a portion of the blood flow in the artery is redirected to flow directly from the artery to the vein. This procedure is usually performed in the arm, above or below the elbow, though may be performed at any of several locations along the upper extremity. There are conventionally three types of AVF: radiocephalic, between a radial artery and a cephalic vein in the forearm region; brachiocephalic, between a brachial artery and a cephalic vein in the upper arm; and brachiobasilic, between a brachial artery and a basilic vein in the upper arm. Furthermore, though FIG. 2a shows a side-to-side connection of an artery and a vein, it is noted that the AVF may instead be formed with an end-to-side connection in which an end of a vein is joined to the side of an artery, as shown in FIG. 1. An AVG method, as seen in FIG. 2b, is largely similar to the AVF method with the exception that, rather than attaching the borders of the separate openings in the artery and the vein directly to one another, a prosthetic graft is inserted as a bridge between the two openings, with the graft forming an end-to-side connection with one end of the graft connected to an end of a vein and another end of the graft connected to a side of an artery.

Once an AVJ is created, both the artery and the vein are subjected to marked changes in hemodynamic forces that trigger vascular remodeling. This remodeling is commonly referred to as "maturation", and it occurs as a result of the changed physiological conditions that accompany formation of the AVJ and the arteriovenous blood flow therethrough, with the vein now being subject to a higher blood pressure from the arterial blood flow. Under normal physiological conditions, the venous system has low pressure-low flow rate properties; however, after formation of an AVJ, pressure in the vein is now exposed to the high pressure-high blood flow arterial system. As a result of the increased blood flow rate and pressure, the vein downstream of the AVJ expands in diameter and the walls thereof thicken.

Before a patient may undergo hemodialysis, a determination must first be made that the location for the vascular access has adequately matured based on predetermined physiological parameters, such as a threshold blood flow rate, a threshold vessel diameter, and a threshold vessel wall thickness. Full maturation typically takes two to four months, at which time the vein will have a suitable blood flow rate within the target range for dialysis, as well as a vessel diameter and wall thickness suitable for reliably accommodating large hemodialysis needles, or other access means for withdrawing and returning a blood flow. Once the blood vessel has fully matured, dialysis sessions will generally take place thrice a week, for four hours each session.

However, while maturation of the blood vessel is desirable for achieving threshold structural characteristics suitable for supporting hemodialysis treatments, this maturation process also presents certain complications. In particular, as the AVJ provides a permanent bridge between the artery and the vein, the vein is thereafter constantly subjected to an increased blood flow rate and pressure from the arterial blood flow. As a result, the blood flow rate in the vein, downstream of the AVJ, typically increases well beyond the target threshold required for dialysis. This increased blood flow rate presents a number of health risks, including: increased cardiac output and cardiac diseases; steal syndrome and/or ischemia; upper arm stenosis; and aneurysm formation. It is estimated that about 30% of successful kidney transplants fail after five years, with a 50% failure rate after ten years. Given these elevated risks the ligation of an AVJ, is commonly not performed unless the patient is at life-threatening risk leaving the patient exposed to the said complications while the AVJ isn't required.

Thus, despite the advances provided to date in the art, there remains a need for improvements to hemodialysis treatments, and in particular the formation and maintenance of AV junctions that may mitigate the risks associated with increased blood flow rates that conventionally result therefrom.

SUMMARY OF THE INVENTION

A blood flow regulator comprises a sheath assembly and a pump assembly. The sheath assembly comprises an inflatable body, the sheath being configured for wrapping around a blood vessel with the inflatable body positioned for constricting a diameter of the blood vessel upon inflation; and a pump assembly comprises a reservoir and a fluid circuit, the reservoir storing a fluid and the fluid circuit being configured to control an exchange of fluid between the reservoir and the sheath for inflating and deflating the inflatable body.

The sheath further comprises a frame that surrounds an outer surface of the inflatable body, the frame being adapted to influence expansion of the inflatable body to promote expansion of the inflatable body in an inward direction to constrict a blood vessel. The frame is made of an elastic material that accommodates variations in pulsatile flows through a blood vessel around which the sheath is wrapped.

A coating element encloses the frame and acts as a barrier between the inflatable body and the frame.

The fluid circuit of the pump comprises a discharging path for discharging a fluid flow from the reservoir to the inflatable body, and a return path for returning a fluid from the inflatable body to the reservoir, the discharging path and return path differing from one another. The discharge path is configured to discharge multiple fluid flows from the reservoir to the inflatable body in discrete volumes for incremental inflation of the inflatable body. An actuable-surface in the form of an elastic dome is provided for controlling fluid flow through the discharge path, the elastic dome being configured to control the opening of first and second pressure valves for sequentially delivering discrete volumes of fluid to the inflatable body and drawings discrete volumes of fluid from the reservoir. The return path is configured to immediately return substantially all fluid stored in the inflatable body to the reservoir in a single activation for rapidly deflating the inflatable body. An actuable-surface in the form of a pressure button that controls fluid flow through the return path is configured to control opening of a pressure valve to provide an unobstructed fluid passage between the inflatable body and the reservoir.

A vascular lumen is configured to incorporate a blood flow regulator according to the present invention by positioning the sheath on a vascular lumen, adjacent to an arteriovenous junction. The vascular lumen may be either a native blood vessel or a non-native artificial graft. When positioned on a blood vessel, the sheath is positioned on a vein at a downstream position, in a blood flow direction, from an anastomosis that provides a blood flow connection between the vein and an artery. When used with an arteriovenous graft, the sheath may instead be positioned on the graft that joins the artery and the vein, with the sheath positioned at either end of the graft or an apex thereof.

In use, a blood flow regulator positioned on a vascular lumen may be actuated to discharge a fluid flow from the reservoir to the sheath for inflating the inflatable body to constrict the vascular lumen for reducing a blood flow rate; and may also be actuated to return a fluid flow from the sheath to the reservoir for deflating the inflatable body to release a constriction on the vascular lumen for increasing a blood flow rate. When used as part of a hemodialysis treatment, the fluid circuit is actuated to return fluid from the sheath to the reservoir to deflate the inflatable body and release a constriction on a vascular lumen for increasing a blood flow rate in preparation for treatment; and, following conclusion of the treatment, the fluid circuit is actuated to discharge a fluid flow from the reservoir to the sheath for inflating the inflatable body to again constrict the vascular lumen and reduce a blood flow rate.

Both the foregoing general description and the following detailed description are exemplary and explanatory only and are intended to provide further explanation of the invention as claimed. The accompanying drawings are included to provide a further understanding of the invention; are incorporated in and constitute part of this specification; illustrate embodiments of the invention; and, together with the description, serve to explain the principles of the invention.

BRIEF DESCRIPTION OF THE DRAWINGS

Further features and advantages of the invention can be ascertained from the following detailed description that is provided in connection with the drawings described below:

FIGS. 8a-8c show further examples of an inflatable body in the sheath of the blood flow regulator in FIG. 3, with inclusion of an exhaust port, including: (a) an inflatable body in an empty state; (b) an inflatable body in an overflow state exhausting fluid into surrounding tissues; and (c) an inflatable body in an overflow state exhausting fluid into an overflow collection chamber;

FIGS. 13a-13e show the pump in the blood flow regulator in FIG. 12, in a non-actuated state, as seen in several views, including: (a) a perspective view of the pump designating several cross-section views; (b) a cross-section view as seen along line b-b in FIG. 13a; (c) a cross-section view as seen along line c-c in FIG. 13a; (d) a cross-section view as seen along line d-d in FIG. 13a; and (e) a cross-section view as seen along line e-e in FIG. 13a;

DETAILED DESCRIPTION OF THE INVENTION

Figures 1, 2A, 2B:
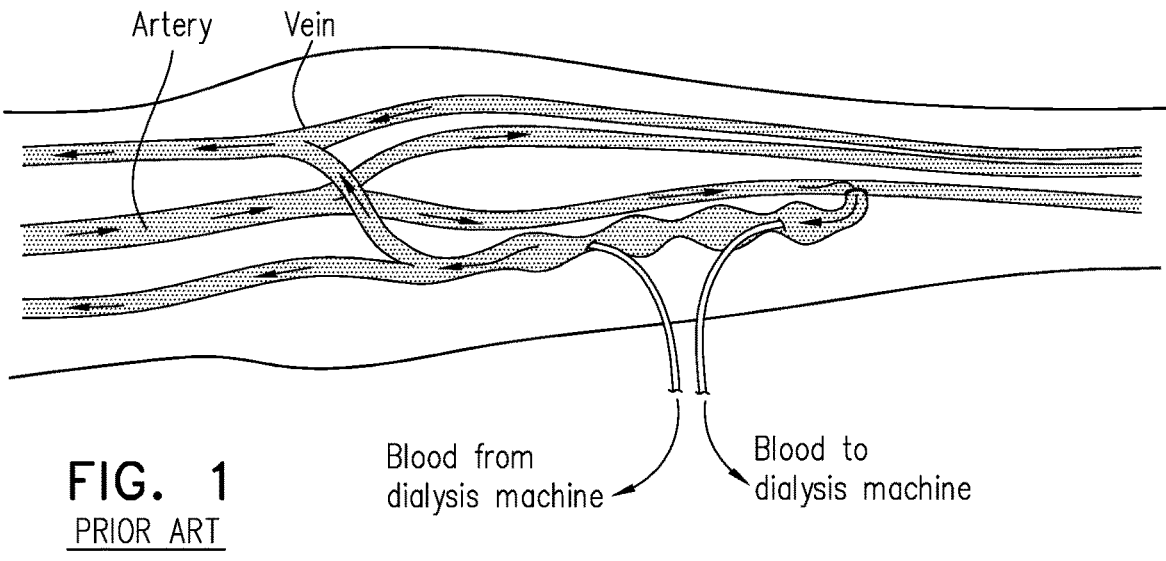
FIG. 1 shows a conventional vascular access for use in a hemodialysis treatment.
FIGS. 2a-2b show conventional examples of arteriovenous junctions, in the form of: (a) an arteriovenous fistula; and (b) an arteriovenous graft.

The following disclosure discusses the present invention with reference to the examples shown in the accompanying drawings, though does not limit the invention to those examples.

The use of any and all examples, or exemplary language (e.g., "such as") provided herein is intended merely to better illuminate the invention and does not pose a limitation on the scope of the invention unless otherwise claimed. No language in the specification should be construed as indicating any non-claimed element as essential or otherwise critical to the practice of the invention, unless made clear in context.

As used herein, the singular forms "a," "an," and "the" include plural referents unless the context clearly dictates otherwise. Unless indicated otherwise by context, the term "or" is to be understood as an inclusive "or." Terms such as "first", "second", "third", etc. when used to describe multiple devices or elements, are so used only to convey the relative actions, positioning and/or functions of the separate devices, and do not necessitate either a specific order for such devices or elements, or any specific quantity or ranking of such devices or elements.

The word "substantially", as used herein with respect to any property or circumstance, refers to a degree of deviation that is sufficiently small so as to not appreciably detract from the identified property or circumstance. The exact degree of deviation allowable in a given circumstance will depend on the specific context, as would be understood by one having ordinary skill in the art.

Use of the terms "about" or "approximately" are intended to describe values above and/or below a stated value or range, as would be understood by one having ordinary skill in the art in the respective context. In some instances, this may encompass values in a range of approx. +/−10%; in other instances, there may be encompassed values in a range of approx. +/−5%; in yet other instances values in a range of approx. +/−2% may be encompassed; and in yet further instances, this may encompass values in a range of approx. +/−1%.

It will be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless indicated herein or otherwise clearly contradicted by context.

As used herein, the term "vascular lumen" will be understood as referring to the interior of a tubular structure within a vascular system that carries a blood flow, including native lumens such as blood vessels and non-native lumens such as artificial grafts.

As used herein, the terms "arteriovenous junction", "AV junction" and "AVJ" will be understood as referring to vascular reconstructions that are adapted for redirecting a blood flow from a first vascular lumen to a second vascular lumen (e.g., from an artery to a vein), including though not limited to an arteriovenous fistula (AV fistula, or AVF) and an arteriovenous graft (AV graft, or AVG).

Recitations of a value range herein, unless indicated otherwise, serves as a shorthand for referring individually to each separate value falling within the stated range, including the endpoints of the range, each separate value within the range, and all intermediate ranges subsumed by the overall range, with each incorporated into the specification as if individually recited herein.

Unless indicated otherwise, or clearly contradicted by context, methods described herein can be performed with the individual steps executed in any suitable order, including: the precise order disclosed, without any intermediate steps or with one or more further steps interposed between the disclosed steps; with the disclosed steps performed in an order other than the exact order disclosed; with one or more steps performed simultaneously; and with one or more disclosed steps omitted.

The present invention is inclusive of an implanted, closed-system blood flow regulator that is configured for constricting vascular lumens to regulate the blood flow in a vascular system; and which is adapted for use in modifying a blood flow rate through a blood vessel proximate to an AVJ. Blood flow regulators according to the present invention are inclusive of a vascular fitment adapted for implantation at a vascular lumen and a flow controller. The vascular fitment comprises an adjustable flow restrictor that is adapted for influencing a blood flow rate through the vascular lumen and a protective frame enclosing the flow restrictor; and the flow controller is adapted to communicate with the vascular fitment for controlling adjustment of the flow restrictor.

Figure 3:
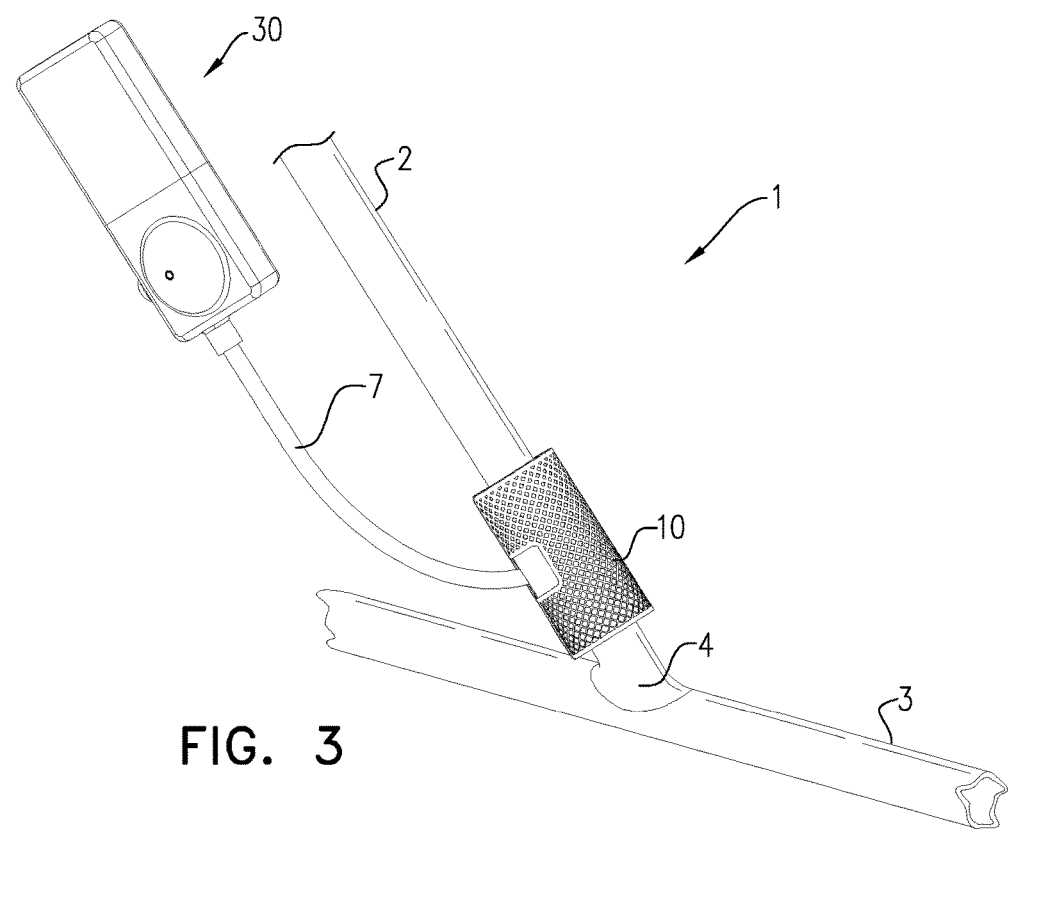
FIG. 3 shows an example of a blood flow regulator according to the present invention.
Figures 4A, 4B:
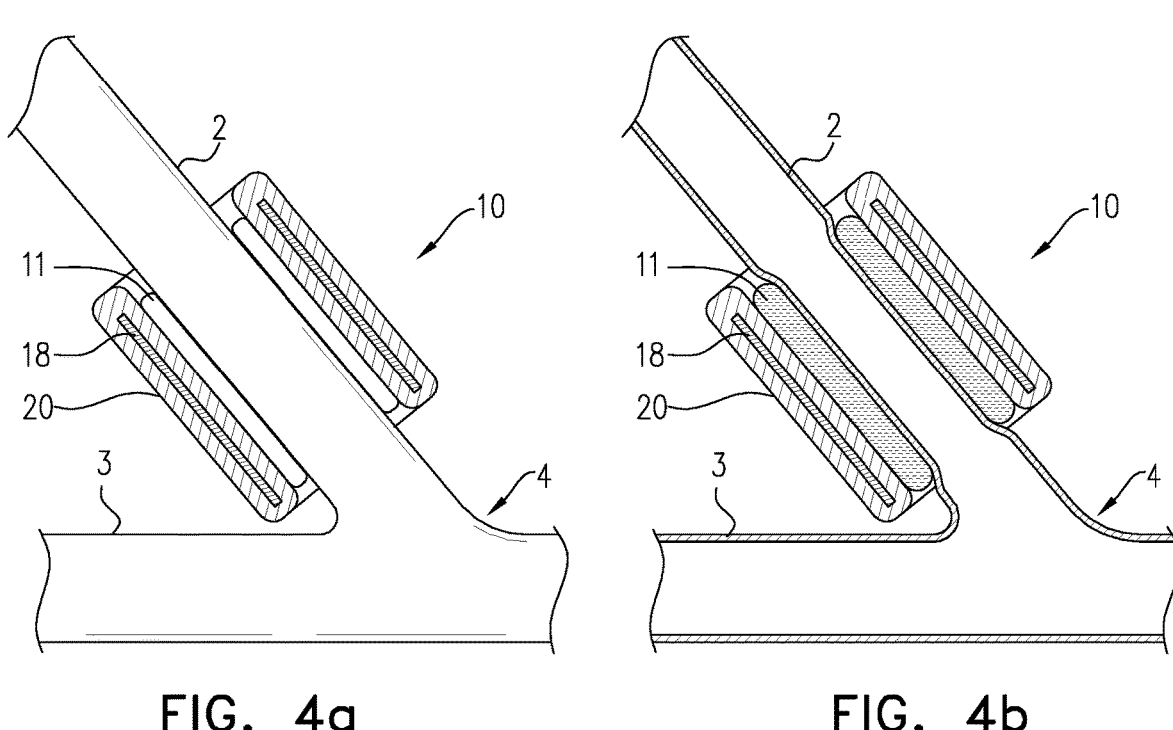
FIGS. 4a-4b show close-up cross-sectional views of the sheath of the blood flow regulator in FIG. 3, in both: (a) a deflated state; and (b) an inflated state.

In the following disclosure, reference is made to an example in which the vascular fitment is embodied by a sheath adapted for placement around an outer circumference of a vascular lumen, with the sheath having a fluid terminal provided in a circumference thereof that runs along an entire length of the sheath. The referenced example also discloses a flow restrictor in the form of an inflatable body that is adapted to receive a fluid flow from a flow controller in the form of a pump comprising a fluid reservoir and a fluid circuit, with the pump communicating with the inflatable body via a fluid conduit. It will be understood, however, that vascular fitments according to the present invention are not limited to sheaths such as those in the referenced embodiments, that flow restrictors are not limited to inflatable bodies such as those in the referenced embodiments, and that flow controllers are not limited to pumps such as those in the referenced embodiments, and that each such element may take other constructions that do not depart from the spirit of the invention. One example of a blood flow regulator 1 according to the present invention is shown in FIG. 3. In the illustrated example, the blood flow regulator 1 comprises a vascular fitment in the form of a sheath 10 for constricting the diameter of a vascular lumen in the form of a vein 2 to control a blood flow rate therethrough, and a flow controller in the form of a pump 30 for controlling constriction at the sheath 10. The pump 30 is in fluid communication with the sheath 10 through a fluid conduit 7. In this example the sheath 10 is positioned on the vein 2 at a downstream location, in a blood flow direction, from an AVJ in the form of an AVF 4 that joins the vein 2 with an artery 3. In use, the sheath 10 is wrapped around a vascular lumen (e.g., vein 2) and the pump 30 is implanted subcutaneously at a sufficiently shallow depth to enable a user to easily manipulate actuable surfaces thereon. FIGS. 4a and 4b show close-up cross-sectional views of the sheath 10 in a deflated state (FIG. 4a), without constriction of the vein 2; and an inflated state (FIG. 4b), with constriction of the vein 2.

Though FIGS. 3-4b show the sheath 10 positioned on a vein 2 at a downstream position (in a blood flow direction) of an AVJ in the form of an AVF 4, it will be understood that the blood flow regulator 1 may instead be used with the sheath 10 positioned on the artery 3 at an upstream position from the AVF 4. It will further be understood that the blood flow regulator 1 may also be used with an AVG with the sheath 10 positioned at any of: a vein, at a downstream position from the graft; an artery, at an upstream position of the graft; or on the graft itself, at either end of the graft or at an apex thereof.

Figures 5A, 5B, 5C:
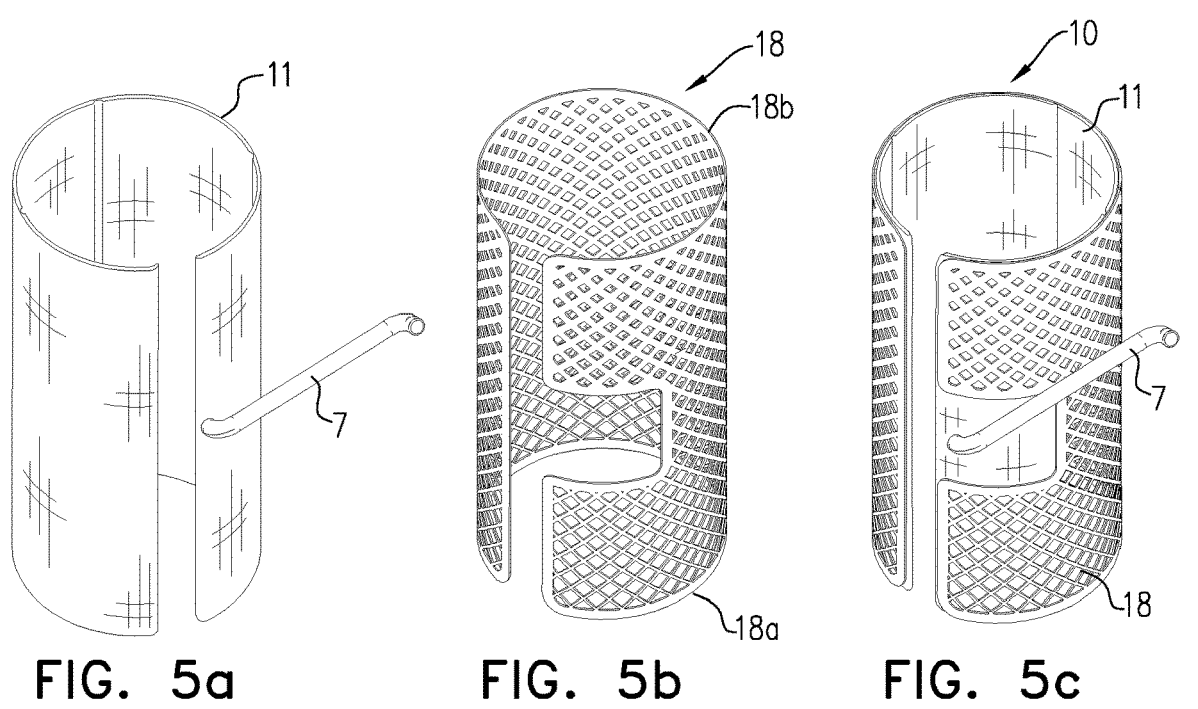
FIGS. 5a-5g show a first example the sheath in the blood flow regulator in FIG. 3, including: (a) a perspective view of the inflatable body; (b) a perspective view of the frame; (c) a perspective view of the combined inflatable body and frame; (d) a cross-sectional view of the inflatable body; (e) a plan view of the frame; (f) a perspective view of the inflatable body in an inflated state; and (g) a cross-sectional view of the inflatable body, as seen along line g-g in FIG. 5f.
Figures 5D, 5E:
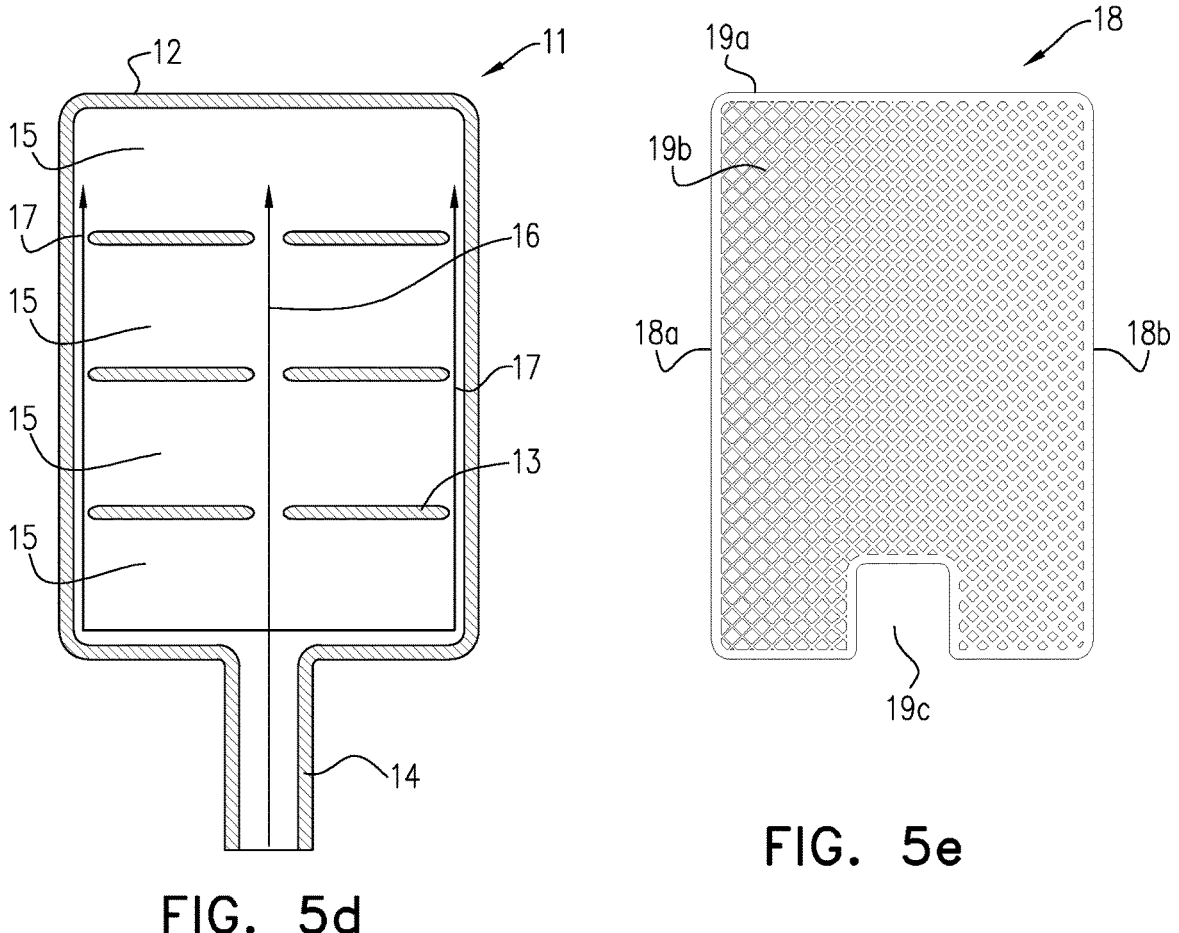
Figure 5G:
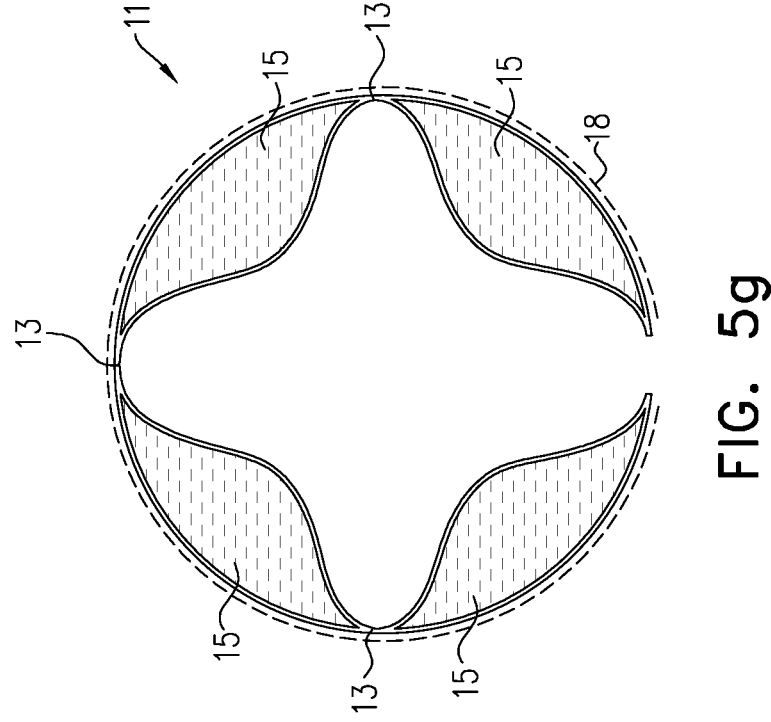
Figure 5F:
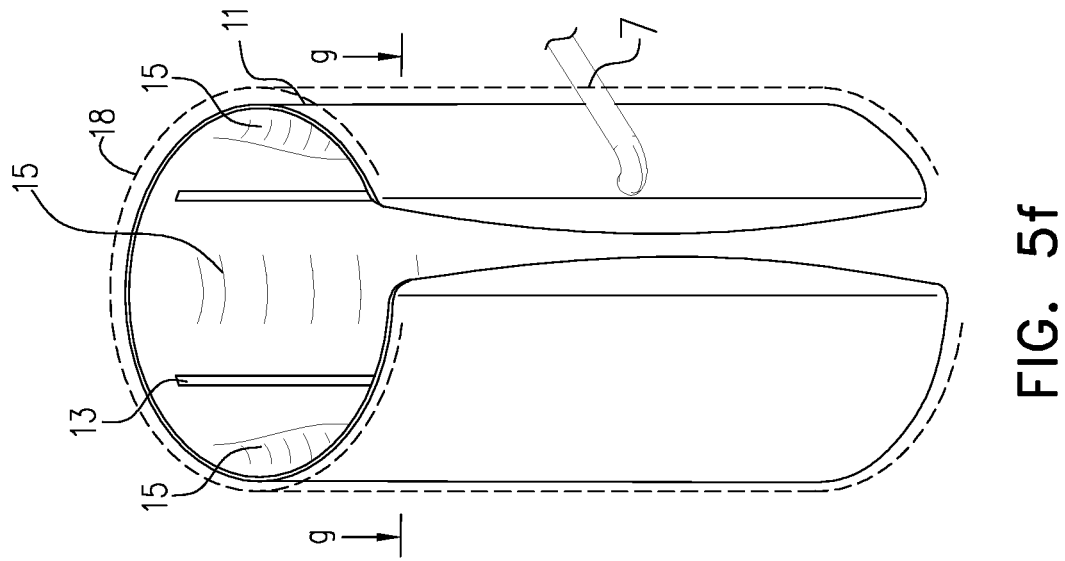

The sheath 10 comprises a flow restrictor in the form of a selectively inflatable and deflatable body, a frame, and a thin coating element. FIGS. 5a-5e show an example of the inflatable body 11 and the frame 18. In this example, the inflatable body 11 (FIGS. 5a and 5d) is made of two elastic layers that are fused to one another along a common perimeter 12 to define an interior space, as well as a number of equidistantly spaced ridges 13 within the interior space. As shown in FIG. 5d, a single passage is provided in the perimeter 12 where the two elastic layers remain unfused, forming an open throat 14 for the passage of fluid in and out of the inflatable body 11. In the illustrated example, the elastic layers are heat-fused or ultrasonically welded to form a number of ridgelines 13, with a central break in each ridgeline 13 that is in alignment with the throat 14, so as to form four uniformly dimensioned inflatable regions 15 that are in fluid flow communication with one another along a central channel 16 and peripheral channels 17. With this arrangement, as a fluid flow is introduced into the inflatable body 11 via the throat 14, the spaced ridgelines 13 act as flow barriers that guide the fluid flow to be evenly distributed to the several separate regions 15 so that the inflatable body 11 inflates uniformly at the several separate regions 15, thereby promoting a uniform application of pressure to a vascular lumen on which the sheath 10 is positioned. An example of the inflatable body 11 is provided in FIG. 5f, with FIG. 5g providing a cross-sectional view as seen along line g-g in FIG. 5f to show separation of the inflated regions 15 by ridgelines 13. Though the illustrated example shows the inflatable body 11 having four inflatable regions 15, there may instead be any number of inflatable regions 15.

The frame 18 (FIGS. 5b, 5c and 5e) is provided to protect the inflatable body 11 from damage, such as from piercing by cannulation needles, and to influence expansion of the inflatable body 11 to achieve a targeted compression of a vascular lumen. By placing the frame 18 at an outer side of the inflatable body 11, opposite the vascular lumen, the frame 18 controls expansion of the inflatable body 11 upon inflation, preventing an outward expansion and promoting an inward expansion that constricts and reduces an overall diameter of a vascular lumen. Preferably the frame 18 is made of an elastic material that promotes ease of insertion and flexing thereof by a physician, and preferably a material having a relatively high cycle fatigue so that the frame 18 is sufficiently flexible to adapt to the shape and geometry of the vascular lumen, without restricting, bending, kinking or otherwise deforming the vascular lumen, while also accommodating and remaining durable to repeat variations in pulsatile blood flows through the vascular lumen. Examples of materials suitable for forming the frame 18 include, though are not limited to polyethylene terephthalate (PET), polytetrafluoroethylene (ePTFE), nylon, polypropylene, cobalt-chromium, polyether ether ketone (PEEK), thermoplastic polyurethane (TPU), and a nickel-titanium composition known as Nitinol.

As shown in FIG. 5e, the frame 18 may be provided in the form of a mesh screen 19a having a number of pores 19b formed therein. The pores are dimensioned to resist the passage of a cannulation needle to thereby protect against piercing of the inflatable body positioned at an interior side of the frame 18. In the illustrated example, the mesh screen 19a is made with pores 19b of varying size, with relatively larger pores provided at a first end 18a of the frame 18a and relatively smaller pores provided at a second end 18b of the frame 18, with the pore size gradually decreasing from the larger pore sizes at the first end to the smaller pore sizes at the second end. The frame 18 is also provided with a cut-away section 19c for accommodating the throat 14 of the inflatable body 11. Though FIG. 5e shows an example of a frame 18 with a variable pore size, it will be understood that the frame 18 may instead be constructed with a mesh structure having pores of uniform size throughout.

A frame 18 with a variable pore size may provide benefits in balancing flexibility of the frame 18 and protection to the inflatable body 11. For example, without being bound by theory, it is expected that a risk of puncture to the inflatable body 11 is greater at an end of the sheath 10 that is further downstream from the AVJ (i.e., a distal end, closer to the heart), as it is common practice to cannulate a vein at superficial locations (e.g., close to the skin surface), which are generally downstream from the AVJ. As such, a sheath 10 having a frame 18 with a variable pore size such as that shown in FIG. 5d, may enable implantation of the sheath 10 on a vein with the frame 18 oriented with the first end 18a positioned closer to the AVJ 4 and the second end 18b positioned further from the AVJ. With such an orientation, the more densely arranged smaller pores at the second end 18b will provide a more protective structure at and end of the sheath 10 that is expected to be at greater risk of puncture by a needle, while the larger pores at the first end 18a will provide more flexibility to the sheath 10 near to the AVJ to further accommodate variations in pulsatile blood flows that are expected to result from redirecting the elevated arterial blood flow into the vein 2.

As shown in FIG. 5e, as well as FIGS. 4a and 4b, the frame 18 is preferably provided as a mesh structure (FIG. 5e) and a coating 20 is applied thereto (FIGS. 4a and 4b) to further protect the inflatable body 11 from damage by external sources as well as potential damage from the frame 18 itself (e.g., friction between the frame and inflatable body). With the frame 18 provided as a mesh structure, the coating 20 may be applied to entirely encapsulate the frame 18 with the coating 20 distributed through the pores of the mesh structure. Alternatively, the coating 20 may be applied only to an interior surface of the protective frame 18, as an intermediate layer between the frame 18 and the inflatable body 11. The coating 20 further promotes a uniform heat fusion, radio-frequency or ultrasonic welding for adhering the inflatable body 11 to the frame 18.

Figures 6A, 6B, 6C:
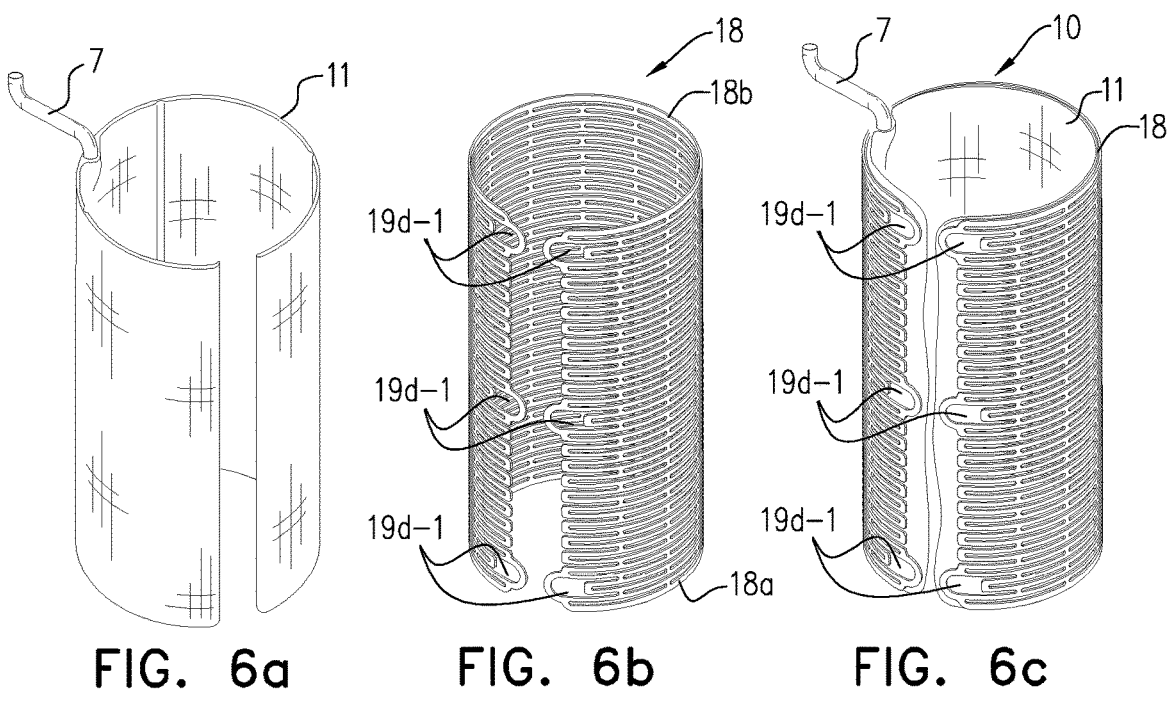
FIGS. 6a-6h show further examples of the sheath in the blood flow regulator in FIG. 3, including: (a) a perspective view of the inflatable body; (b) a perspective view of the frame; (c) a perspective view of the combined inflatable body and frame; (d) a cross-sectional view of the inflatable body; (e) a plan view of the frame; (f) a construction of the frame with first alternate closure mechanisms; (g) a construction of the frame with second alternate closure mechanisms; and (h) a construction of the frame with a tapered body.
Figures 6D, 6E:
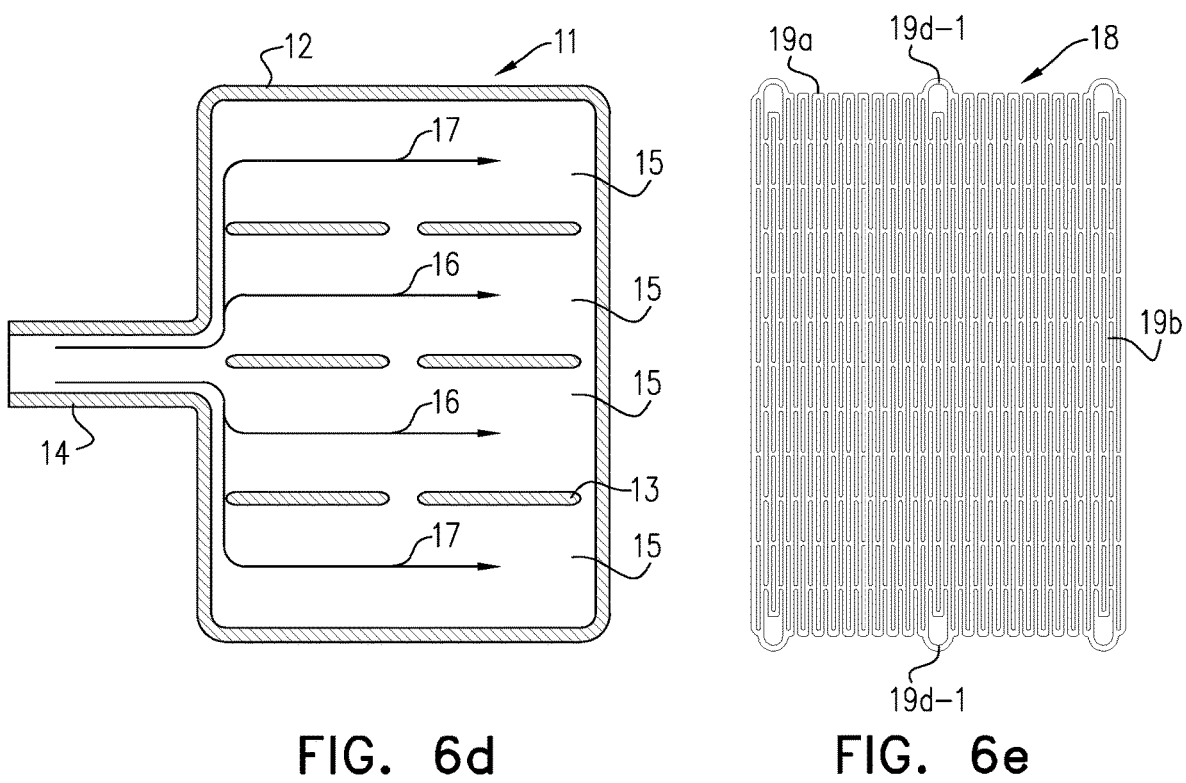

FIGS. 6a-6e show another example of the inflatable body 11 and the frame 18. In this example, the inflatable body 11 (FIGS. 6a and 6d) is made with a similar construction as that discussed above (as shown in FIGS. 5a and 5d), with the exception that the throat 14 is provided along a lateral side of the periphery 12, rather than an opposing end. The inflatable body 11 in this example may adopt the same arrangement as the ridgelines 13 as discussed in the foregoing example, or may adopt an alternative arrangement as shown in FIG. 6d. In this alternative arrangement, the ridgelines 13 are oriented to extend in a common direction with the throat 14, thereby reducing a resistance against a fluid flow received through the throat 14, while still promoting a disbursed flow of fluid to several separate regions 15 for a uniform inflation of the inflatable body 11.

The frame 18 in this alternative example (FIGS. 6b, 6c and 6e) is generally made with a similar construction as that discussed above (as shown in FIGS. 5b, 5c and 5e), though with a number of differences. As the inflatable body 11 in this example has a throat 14 along a lateral periphery thereof, the frame 18 in this example (FIGS. 6b, 6c and 6e) may forego inclusion of a cut-away section (as in FIG. 5e, at 19c). Whereas the frame 18 in the former example includes a mesh screen construction 19a having pores 19b of varying size, the frame 18 in this example is provided with a mesh screen construction 19a having pores 19b of uniform size.

Figures 6F, 6G, 6H:
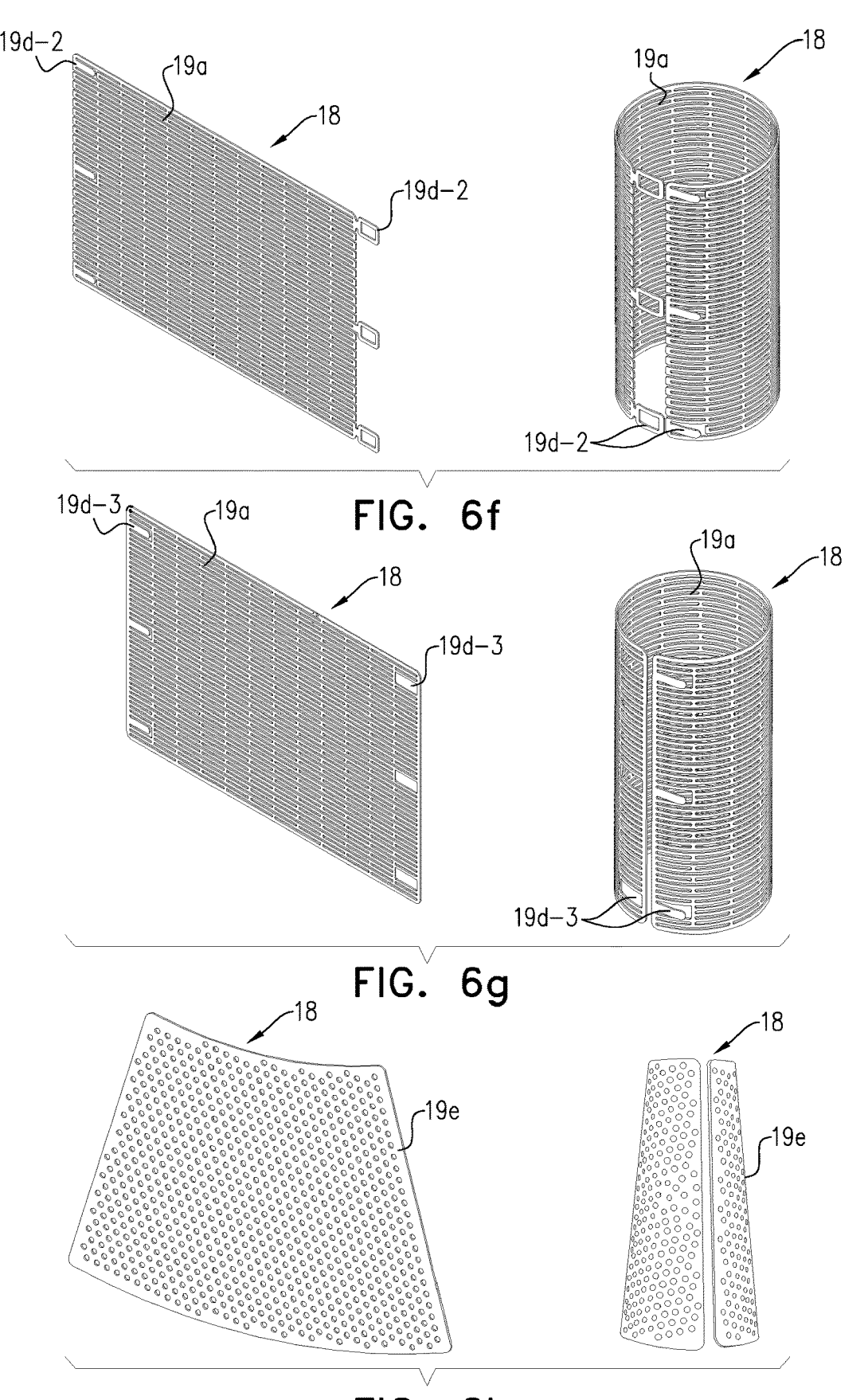

In this example, the frame 18 is provided with closure mechanisms for joining opposing ends of the frame 18 to one another after positioning the sheath 10 on a vascular lumen, thereby further preventing biased inflation of the inflatable body 11 in an outward direction. In the example shown in FIGS. 6b, 6c and 6e, the closure mechanisms 19d-1 are provided in the form of eyelets that are dimensioned for reception of sutures to join opposing pairs of eyelets to one another. In the examples shown in FIGS. 6f and 6g, the closure mechanisms (19d-2 in FIG. 6f, and 19d-3 in FIG. 6g) are provided in the form of mating hooks-and-eyes, with hooks at a first end of the frame 18 sized for reception in corresponding eyes at a second end of the frame 18. FIG. 6f shows an example in which the closure mechanisms 19d-2 includes eyes that are made to protrude from the periphery of the frame 18, and FIG. 6g shows an example in which the closure mechanisms 19d-3 include eyes that are formed within the mesh screen 19a of the frame 18. In other, non-limiting examples, the closure mechanisms may be provided in the form of zip locks, latches, straps, clips, or any combination of these and the foregoing examples. With inclusion of a closure mechanism, a sheath that is initially provided with a pre-curved construction (e.g., a C-shape construction), such as those shown in FIGS. 5c, 6c, 6f and 6g, may effectively be made to have an O-shaped arrangement that fully surrounds a circumference of a vascular lumen upon implanting the sheath 10 around a vascular lumen and engaging opposing pairs of closure mechanisms within one another.

FIG. 6h shows an alternative construction of the frame 18. In this example, rather than a mesh screen, the frame 18 is instead formed as a sheet 19e have a number of pores formed therein. Also in this example, the frame 18 is made to have a tapered construction such that, upon implantation and enclosure around a vascular lumen (e.g., a vein 2), the frame 18 promotes a conical shaping of the sheath 10 therearound.

Examples of suitable materials for the coating 20 include, though are not limited to a thin layer thermoplastic elastomers (TPE) such as styrenic block copolymers (TPS), thermoplastic polyolefin elastomers (TPO), thermoplastic vulcanizates (TPV), thermoplastic polyurethanes (TPU), thermoplastic copolyesters (TPC or TPE-E), thermoplastic polyamides (TPA or TPE-A) and unclassified thermoplastic elastomers (TPZ). As another alternative, the coating 20 may be formed from a thermoset elastomer (TSE), such as liquid silicone rubber (LSR). The coating may be produced by any suitable method, including though not limited to injection molding, casting and coating. Preferably, the coating 20 has the same or similar mechanical properties as the inflatable body 11, and more preferably is made of the same material as the inflatable body 11, for further promoting adhesion. Coating methods may include, though are not limited to, brushing, dip-coating, spraying, and spin coating the frame 18 with a coating material in a liquid state with subsequent hardening of the coating material to a solid state to form the coating.

Figure 7:
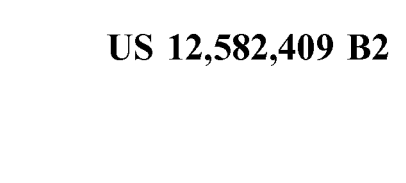
FIG. 7 shows a view of the interior surfaces of the inflatable body in the sheath of the blood flow regulator in FIG. 3, with textured interior surfaces for resisting adhesion upon contact of opposing surfaces.

The inflatable body 11 may be made of the same materials as the coating 20, with the coating and the inflatable body then having the same mechano-chemical properties for further promoting a reliable bond between the inflatable body 11 and the coating 20, and in turn strengthening a bond of the inflatable body 11 to the frame 18. For example, it is preferred that the materials be bondable (e.g., by fusion, welding, adhesives, etc.), that the materials share similar elasticity, bending moments, fatigue effects on the adhesion of the two, and that they have low abrasion. Preferably, the inflatable body 11 is made with inner and outer surfaces having different texture characteristics. As shown in FIG. 7, inner surfaces of the inflatable body 11 are preferably made to have relatively roughened, non-uniform textures 11b with irregularities along the surface. This roughened texture 11b is preferred so that in the event two internal surfaces come in contact with one another, such as when the inflatable body 11 is deflated, there may remain pathways for fluid flow between the two surfaces, such that there is a reduced likelihood that the two internal surfaces adhere to one another and/or otherwise block a fluid flow through the inflatable body 11. Outer surfaces of the inflatable body 11 are preferably made to have a relatively smoothened, uniform texture 11c with a low friction characteristic. This smoothened surface texture 11c is preferred for reducing friction between the inflatable body 11 and a vascular lumen against which the inflatable body 11 when the inflatable body 11 is inflated and deflated. In some examples, the inflatable body 11 may be made to have the different surface characteristics through a construction using multiple layers of materials. The multiple layers may further comprise a diffusion resistive layer that resists diffusion of a fluid flow contained within the inflatable body 11 to mitigate the passage of fluid molecules (e.g., gas or liquid molecules) through pores in the inflatable body 11.

FIGS. 8a-8c show further examples of the inflatable body 11 that include an exhaust valve 12a that limits inflation of the inflatable body 11 to a predetermined threshold, for example, corresponding with a predetermined inflation capacity and/or inflation pressure. In this example, the exhaust valve 12a is constructed along the periphery 12 of the inflatable body 11 in the form of a leaf valve that opens to provide a fluid flow path between an interior of the inflatable body 11 and outside of the inflatable body 11. In some examples, as shown in FIG. 8b, the exhaust valve 12a may open to provide a path for a fluid flow to exit the inflatable body 11 for dispersion into the surrounding tissues. In other examples, as shown in FIG. 8c, the exhaust valve 12a may open to provide a path for a fluid flow to exit the inflatable body 11 for dispensing into a separate collection chamber 11a. A collection chamber 11a, when included, may be constructed to retain overflow fluid for subsequent extraction, or may be formed from a diffusible material that enables diffusion of small molecules, such as saline, from an interior of the collection chamber to an exterior of the collection chamber for dispersion into the surrounding tissues.

In use, the sheath 10 is surgically placed around a vascular lumen by a physician inserting a first end of the sheath 10 beside the vascular lumen and wrapping an opposite end of the sheath 10 thereof around the vascular lumen toward the first end of the sheath. In some examples, the sheath 10 may initially be provided in a flattened shape and a physician may flex the sheath 10 to wrap it around the vascular lumen. Alternatively, the sheath 10 may initially be provided in a pre-curved shape with a spacing provided between opposite and opposing ends thereof (e.g., a C-shape), and a physician may flex the sheath 10 to spread the free ends to expand the spacing between the opposing ends for insertion of a vascular lumen within the curvature and placement of the sheath 10 around the vascular lumen.

Figure 9A:
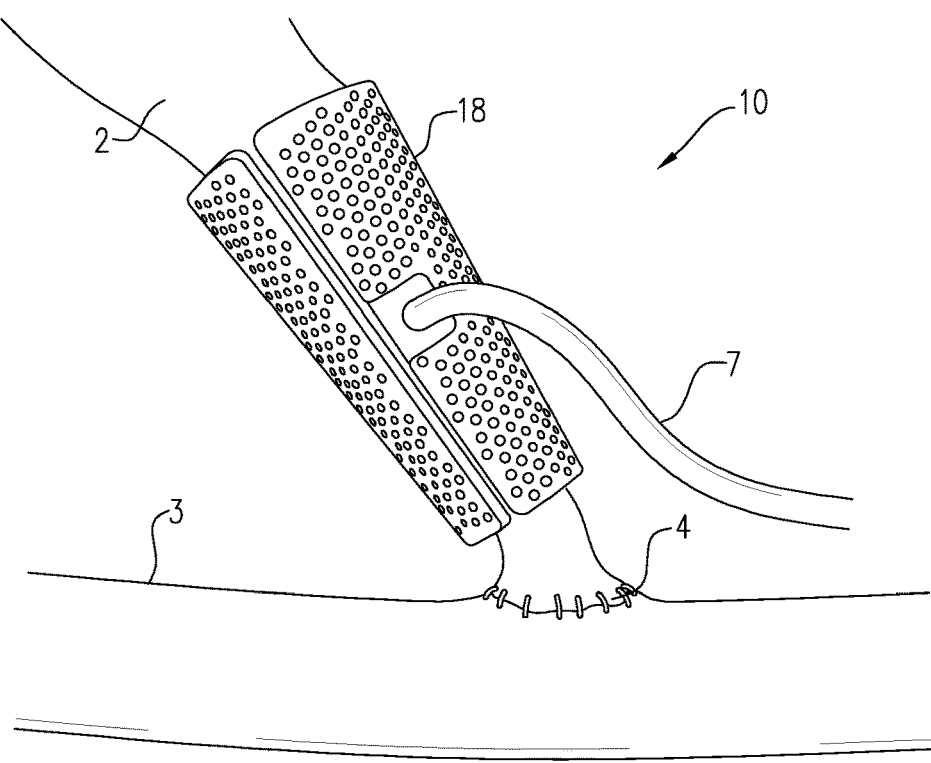
FIGS. 9a-9d show further examples of the sheath 10 of the blood flow regulator in FIG. 3, including: (a) a side elevation view of an implanted sheath 10 with a side-mounted fluid conduit; (b) a side cross-sectional view of an implanted sheath 10 with a side-mounted fluid conduit; (c) a side elevation view of an implanted sheath 10 with an end-mounted fluid conduit; and (d) a side cross-sectional view of an implanted sheath 10 with an end-mounted fluid conduit.
Figure 9B:
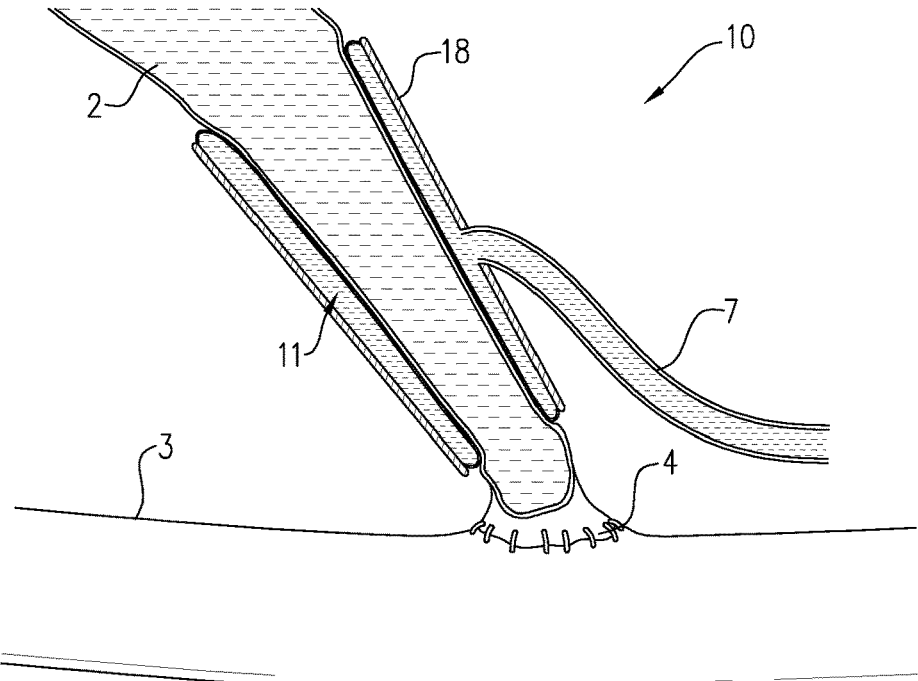
Figure 9C:
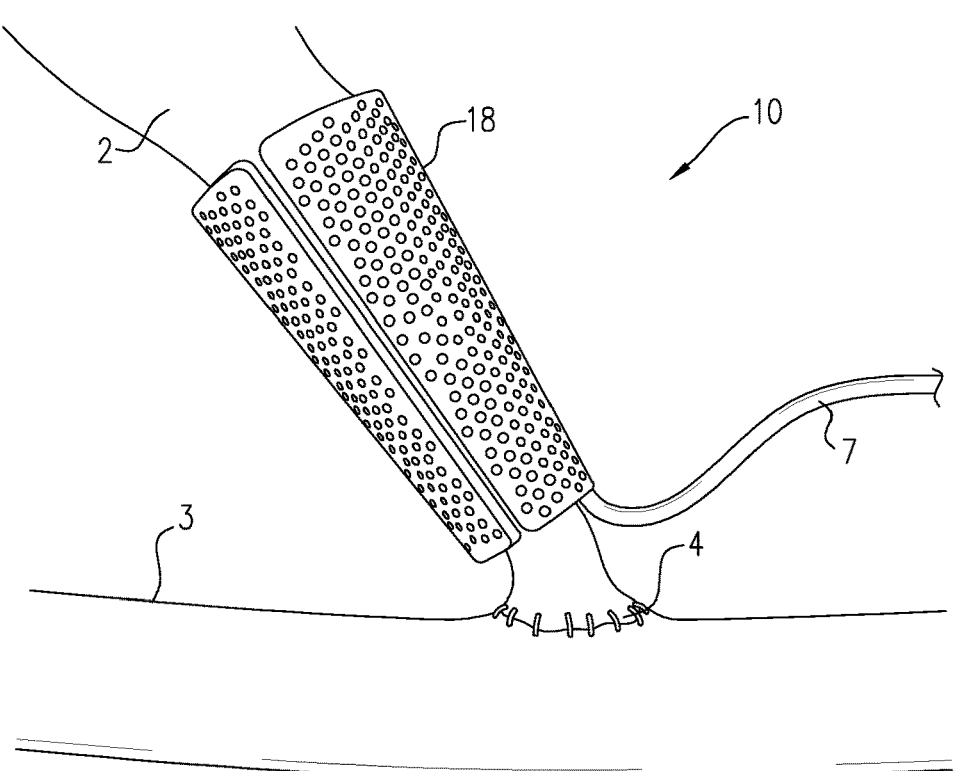
Figure 9D:
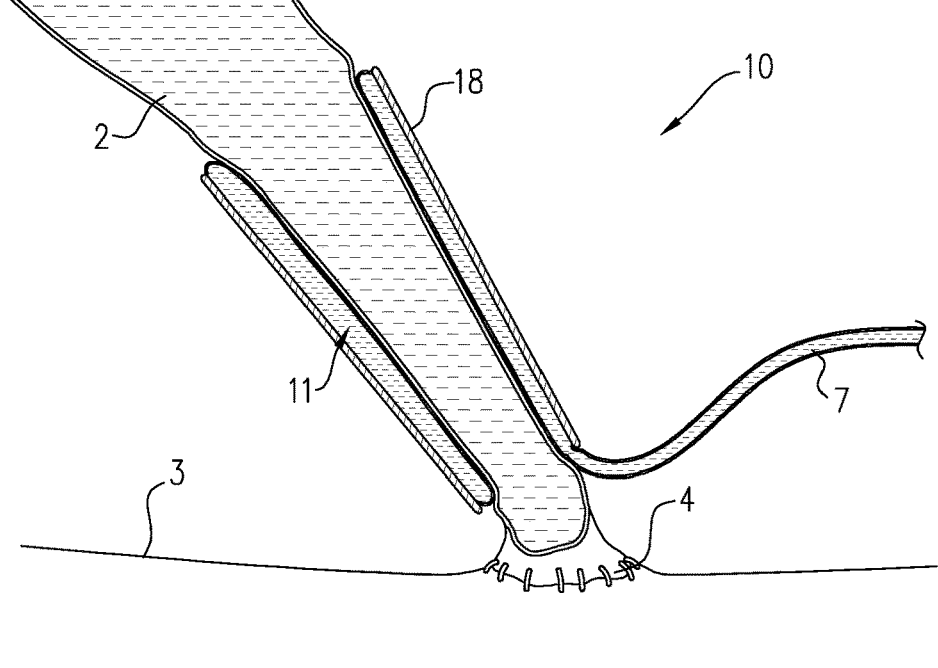

Though the illustrated example shows the sheath 10, including both the inflatable body 11 and frame 18, with a rectangular shape that forms a cylindrical structure around a vascular lumen, it will be understood that the sheath 10 and the individual components thereof may be provided in any suitable shape for best achieving a targeted blood flow control. FIGS. 9a-9b show one example in which the sheath 10 is made with a frame 18 having a tapered construction such that the sheath 10, upon being implanted around a vascular lumen (e.g., a vein 2), presents a tapered conical structure. Likewise, the frame 18 may be provided with a structure other than a mesh screen. For example, as also shown in FIG. 9a, the frame 18 may instead be formed as a sheet have a number of pores formed therein. Again, as with FIG. 3, the coating 20 is omitted from FIGS. 9a-9b to better illustrate the frame 18 and inflatable body 11. In some examples, the inflatable body 11 and frame 18 may be provided with different shapes, with inflation of the inflatable body 11 in the first shape and restriction by the frame 18 in the second shape cooperating to achieve a targeted constriction to a vascular lumen. Computational fluid dynamics analyses may be used to determine optimal shapes of the inflatable body and frame for achieving targeted blood flow regulations. FIGS. 9c-9d show an alternative example of the sheath 10 in which the fluid conduit 7 connects with a throat 14 formed on a lateral side of the inflatable body 11 (as shown in FIG. 6d), rather than an opposing end (as shown in FIG. 5d), resulting in the conduit 7 extending from an end of the sheath 10, rather than a mid-section thereof (as in FIGS. 9a-9b).

Figure 10A:
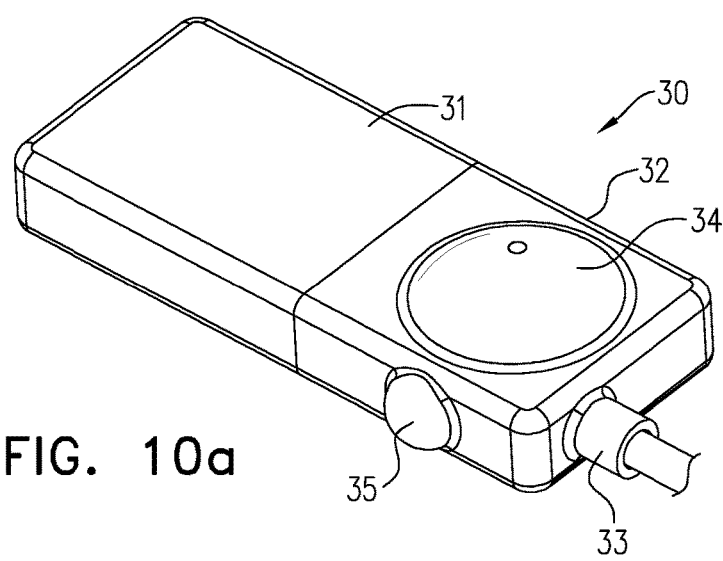
FIGS. 10a-10d show a pump of the blood flow regulator in FIG. 3, including: (a) a perspective view of the pump; (b) a side elevation view of the pump; (c) a first cross-sectional view of the pump, as seen along line c-c in FIG. 10b; and (d) a second cross-sectional view of the pump, as seen along line d-d in FIG. 10b.
Figure 10B:
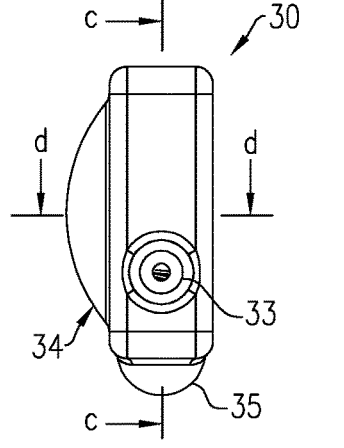
Figure 10C:
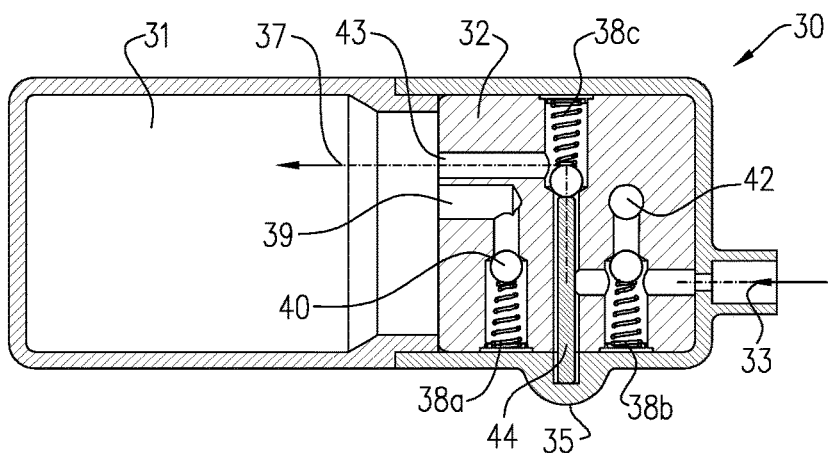
Figure 10D:
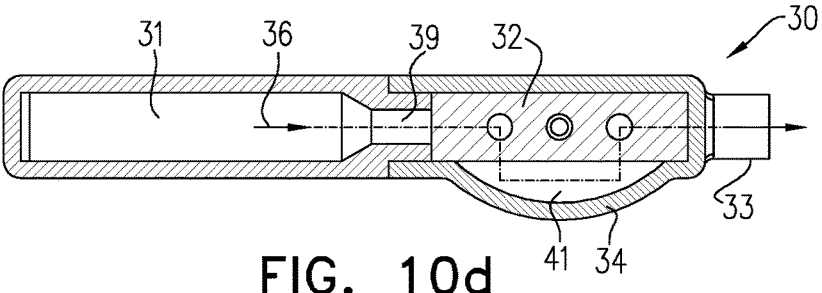

FIGS. 10a-10d show one example of a pump 30 according to the present invention. FIG. 10b shows a side elevation view of the pump 30, FIG. 10c shows a cross-section of the pump 30 along line c-c in FIG. 10b; and FIG. 10d shows a cross-section of the pump 30 along line d-d in FIG. 10b. In this example, the pump 30 comprises an internal reservoir 31 for holding a fluid, a fluid circuit 32 for conveying fluid between the reservoir 31 and a pump throat 33 that is in fluid-communication with the inflatable body throat 14 via the fluid conduit 7, and two actuable surfaces 34/35 for controlling the fluid circuit 32. The reservoir 31 may contain a fluid in the form of either a gas or liquid. In a preferred example, the reservoir 31 contains a liquid fluid comprising medical grade saline, water, oil, glycerol, or a combination thereof.

The fluid circuit 32 comprises two separate fluid paths; a discharging path 36, and a return path 37. The discharging path 36 comprises first and second pressure valves 38a/38b that are responsive to a first actuable surface in the form of an elastic dome 34; and the return path 37 comprises a third pressure valve 38c that is responsive to a second actuable surface in the form of a pressure button 35. In the illustrated example the pressure valves 38a-38c are provided as check valves in which a spring biases a ball bearing toward a position for closing a fluid flow; however, in other examples other pressure valve types may instead be used.

The fluid discharging path 36 is inclusive of a reservoir outlet 39 that communicates with the reservoir 31 and leads to the first pressure valve 38a which controls the passage of fluid from the reservoir 31 through a dome inlet 40 to an inner space 41 of the dome 34; and a dome outlet 42 that communicates with the dome inner space 41 and leads to the second pressure valve 38b which controls the passage of fluid from the dome inner space 41 to the pump throat 33. The fluid return path 37 is inclusive of a passage that communicates with the pump throat 33 and leads to the third pressure valve 38c which controls the passage of fluid to a reservoir inlet 43 that communicates with the reservoir 31.

In operation, a user iteratively inflates the inflatable body 11 by successively compressing the elastic dome 34. On a first compression, a positive pressure is generated on a fluid within the dome inner space 41 and communicated through the dome outlet 42 to momentarily force open the second pressure valve 38b, causing the pressurized fluid in the dome inner space 41 to flow through the second pressure valve 38b, out the pump throat 33 to the fluid conduit 7 that leads to the inflatable body throat 14. Upon relieving pressure thereto, the elastic dome 34 returns to a non-compressed state, the second pressure valve 38b returns to a closed state, and there is created a negative pressure within the dome inner space 34. As the second pressure valve 38b is closing, the negative pressure in the dome inner space 34 is communicated through the dome inlet 40 to at the same time momentarily force open the first pressure valve 38a and draw in a discrete amount of fluid from the reservoir 31 through the first pressure valve 38a and into to the dome inner space 41. This process is repeated upon each successive compression of the elastic dome 34, with fluid pulled to the inner space 41 from the reservoir 31 in a prior compression being delivered to the inflatable body 11, and a further discrete amount of fluid being drawn from the reservoir 31 to the dome inner space 41 for a next compression of the dome 34. With each successive compression of the dome 34, the inflatable body 11 is further inflated and the reservoir 31 is further depleted of fluid, leading to an increasing pressure in the inflated body 11 and a reducing pressure within the reservoir 31 as more fluid is removed therefrom.

A user may deflate the inflatable body 11, and return fluid to the reservoir 31, by applying pressure to a release button 35, which in turn forces open the third pressure valve 38*c* creating a return path 37 between the pump throat 33 and the reservoir inlet 43. In the illustrated example, the release button 35 communicates with a push rod 44 that transfers pressure placed on the button 35 to press a ball bearing against a biasing spring to open the valve. When the return path 37 between the pump throat 33 and the reservoir inlet 31 is opened, pressurized fluid in the inflated body 11 passes immediately through the open return path 37 to the low pressure reservoir 31, rapidly deflating the inflatable body 11.

Preferably, to prevent thrombosis and/or stenosis due to over-inflation of the inflatable body 11, the volume of the reservoir 31 and/or the maximum fluid volume held therein is calibrated based on the physiology of the specific patient receiving the implant. In this way, even if the reservoir 31 is completely emptied, with all fluid transferred to inflating the inflatable body 11, the inflatable body 11 is limited to a maximum inflation that is deemed safe for the particular patient. For example, the reservoir/fluid volume could be limited such that at maximum inflation of the inflatable body 11 there is achieved a minimum vascular lumen diameter of 3 mm, with the inflatable body 11 being incapable of inflating to such a degree to achieve vascular lumen diameters below 3 mm.

It is preferable that inflation of the inflatable body 11 be achieved in iterative steps, with only a discrete amount of fluid transferred from the reservoir 31 to the inflatable body 11 with each actuation. In this way, there is provided a greater degree of sensitivity to flow rate changes made possible with a blood flow regulator according to the present invention, enabling physicians to achieve target blood flow rates with greater accuracy and ease. Preferably deflation of the inflatable body 11 is immediate, with a single press of the release button 35 being operative to transfer substantially all fluid from the inflatable body 11 to the reservoir 31, such that a restriction on blood flow due to constriction of the vascular lumen by the inflated body 11 may be immediately relieved in the event of an urgent need.

Figure 11:
FIG. 11 shows an alternative configuration of a blood flow regulator according to the present invention, this example having a fluid reservoir separate from the pump and provided with an embedded port.

FIG. 11 shows an alternative configuration of a blood flow regulator 1 according to the present invention. As this alternate construction is largely similar to that shown in FIG. 3, discussion is provided here of only the differences between these constructions with an understanding that the foregoing disclosure is likewise applicable to this construction unless otherwise made clear. An initial difference in the example shown in FIG. 11 is that a pump 30 is connected to the sheath 10 via a fluid conduit 7 that communicates with a throat 14 positioned at a lateral side of the inflatable body, as seen in FIG. 6*d*. Another difference is found in that the reservoir 31 in this example is provided as a separate structure positioned remotely from the pump 30 and placed in fluid communication via a second fluid conduit 8 that extends between the pump 30 and the reservoir 31. This alternate configuration provides the additional benefit of enabling selective positioning of the separate pump and reservoir components depending on anatomical limitations when implanting the blood flow regulator 1, on a case-by-case basis.

As shown in FIG. 11, the reservoir 31 may be provided with an embedded port 31*a* for the introduction and/or removal of fluid from the reservoir 31. As shown in the illustrated example, the embedded port 31 may be provided at the reservoir 31 that opens through an exterior surface of the reservoir 31. Such a port 31*a* may be sealed with an elastic membrane that is adapted for piercing by a syringe, though is of sufficient elasticity to enable fluid-tight resealing upon withdrawal of the syringe. Alternatively, the port 31*a* may protrudes sufficiently from the reservoir 31 such that when the reservoir 31 is implanted subcutaneously an outlet of the port 31*a* may protrude from the patient's skin, and may be provided with an access mechanism that can be manipulated to access the reservoir 31. By providing an embedded port 31*a* to the reservoir 31, a physician may make adjustments to the fluid volume contained therein subsequent to implantation, for example, if needing to increase or decrease a fluid volume to effect a corresponding change to the maximum inflation capacity of the inflatable body 11, or if needing to refill the fluid reservoir.

Figure 12:
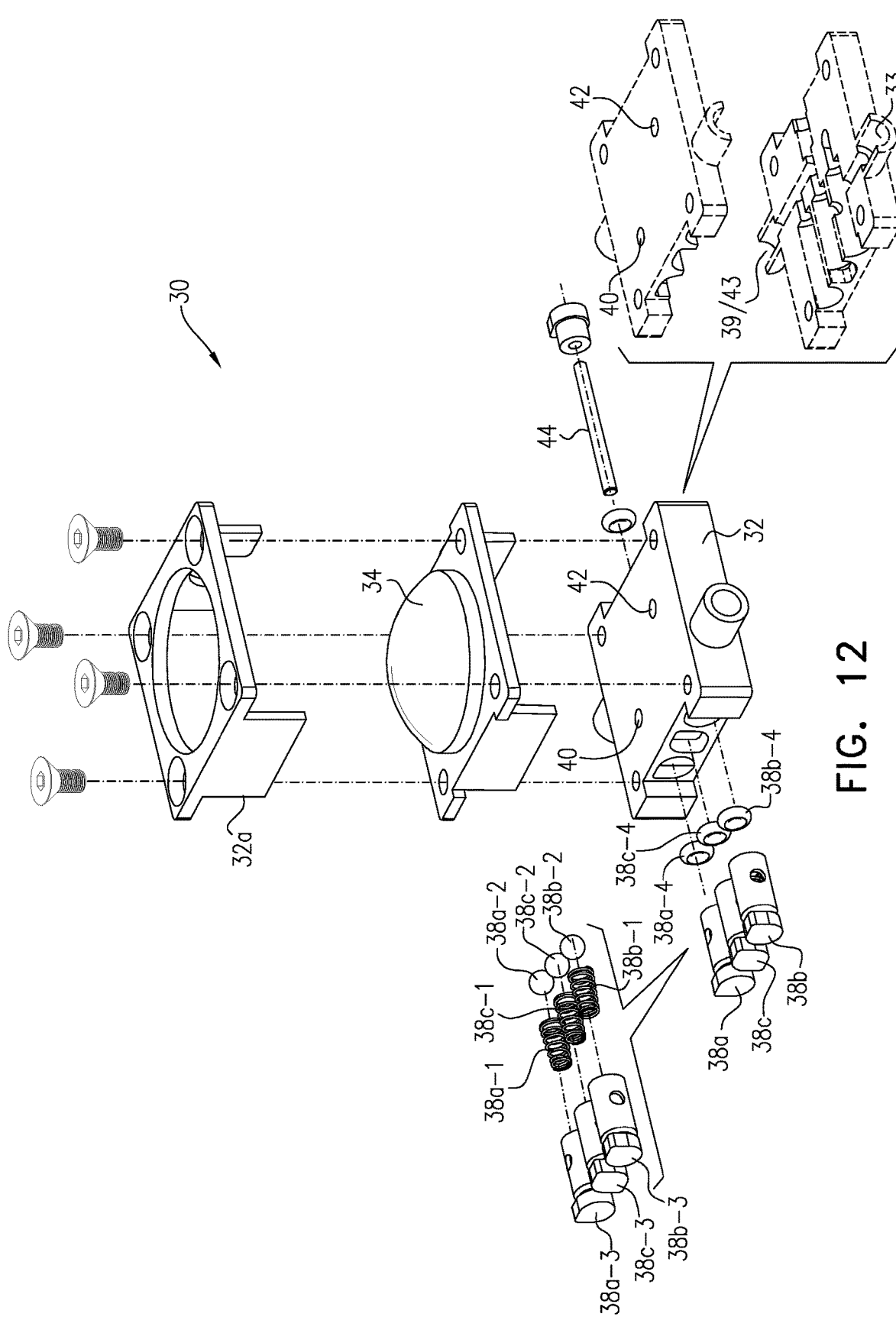
FIG. 12 shows an exploded view of the pump in the blood flow regulator in FIG. 11.

FIG. 12 shows an exploded view of the pump 30 from the alternate construction in FIG. 11. This alternate construction of the pump 30 is nearly identical to that of the prior example, as discussed relative to FIGS. 10*a*-10*d*, with substantially identical functional operation. As such, discussion is provided here of only the differences between these constructions with an understanding that the foregoing disclosure is likewise applicable to this construction unless otherwise made clear. As with the prior example, the pump 30 in this example is likewise inclusive of to actuable surfaces contained within a two-piece housing, including a base component forming the fluid conduit 32 and a dome cover 32*a*, the actuable surfaces again being provided in the form of a dome 34 and a pressure button 35. As also with the prior example, the pump 30 in this example is likewise inclusive of a fluid conduit 32 having first, second and third pressure valves 38*a*, 38*b*, and 38*c* which are each provided with biasing elements (38*a*-1, 38*b*-1, 38*c*-1) and ball bearings (38*a*-2, 38*b*-2, 38*c*-2) contained within respective housings (38*a*-3, 38*b*-3, 38*c*-3) that are each received in the fluid conduit 32 with a fluid tight seal provided by respective o-rings (38*a*-4, 38*b*-4, 38*c*-4). An initial difference in this example, as can be seen in the figures, is that this alternative construction presents a single fluid channel that provides the dual functions of both the reservoir outlet 39 and the reservoir inlet 43, as shown in FIG. 10*c*. This difference in construction does not present any significant difference in operational function, as the function of the dual inlet/outlet opening 39/43 will be dependent on an operational state of the third pressure valve 38*c*.

Generally, as with the prior example, in an inflation actuation, the first pressure valve 38*a* controls a flow of fluid from the fluid reservoir 31, via the reservoir outlet 39, to the dome inner space 41, via the dome inlet 40; and the second pressure valve 38*b* controls a flow of fluid from the dome inner space 41, via the dome outlet 42, to the inflatable body 11 of the sheath 10, via the pump throat 33. As also with the prior example, in a deflation actuation, the third pressure valve 38*c* controls a flow of fluid from the inflatable body 11 of the sheath 10, via the pump throat 33, for delivery to the fluid reservoir 31, via the reservoir outlet 43, when a fluid flow path is formed through the third pressure valve 38*c* to effectively bypass the first and second pressure valves 38*a*, 38*b*. The third pressure valve 38*c* defaults to a closed position preventing the return of a fluid flow through the reservoir inlet 43, and opens a fluid path that permits a return of a fluid flow through the reservoir inlet 43 only upon a user manipulating the actuable surface 35 to open the third pressure valve 38*c*.

Figure 13A:
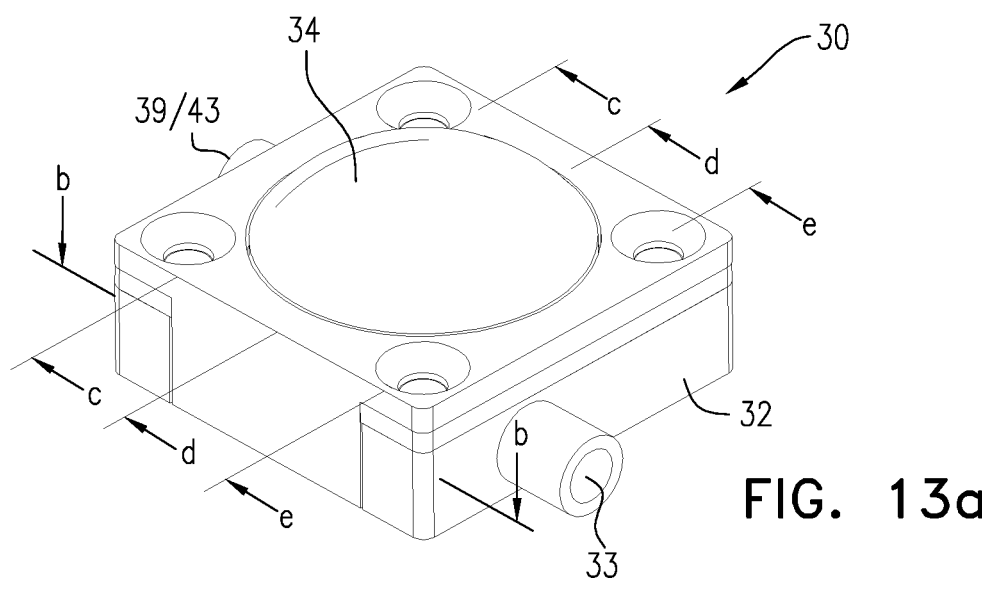
Figure 13B:
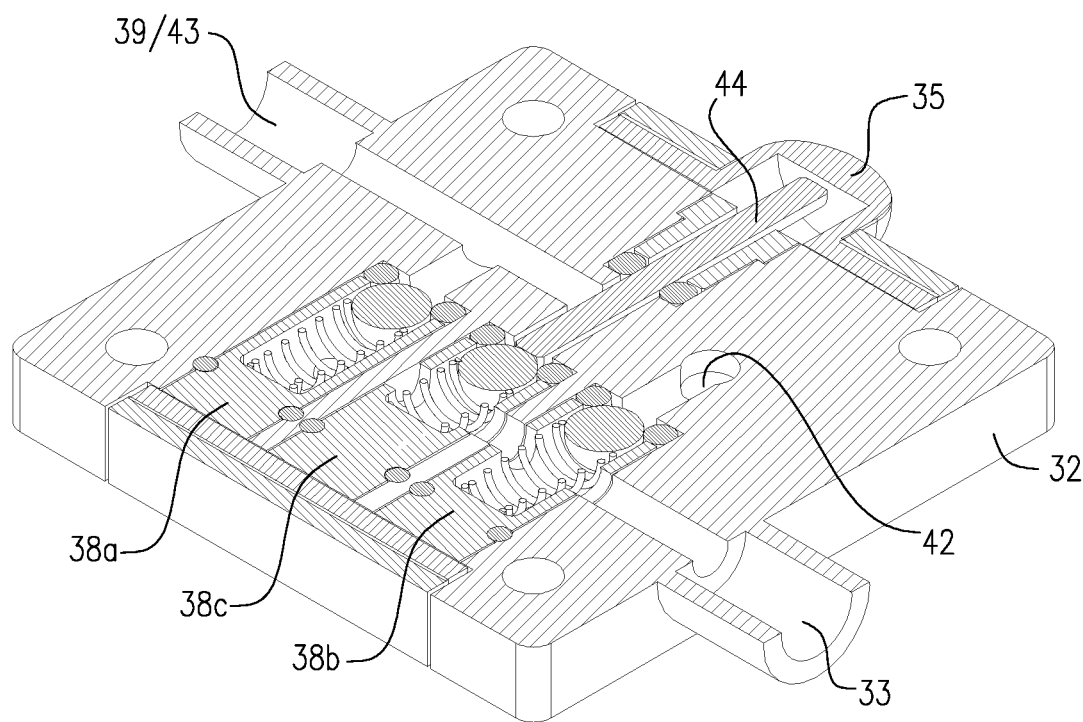
Figure 13C:
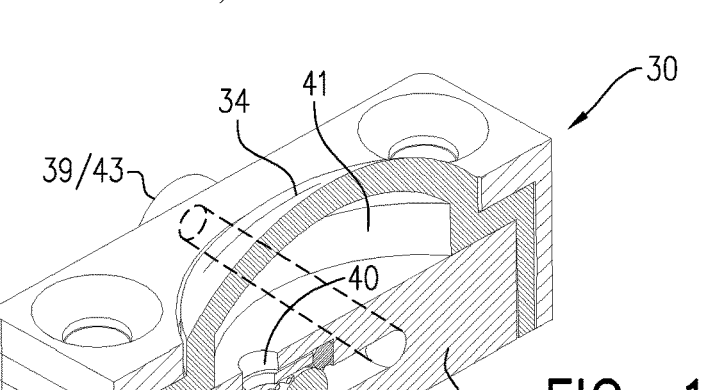
Figure 13D:
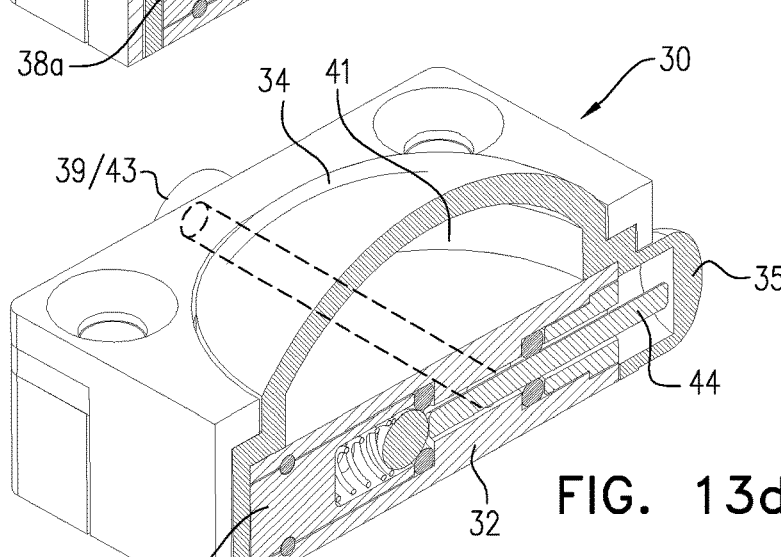
Figure 13E:
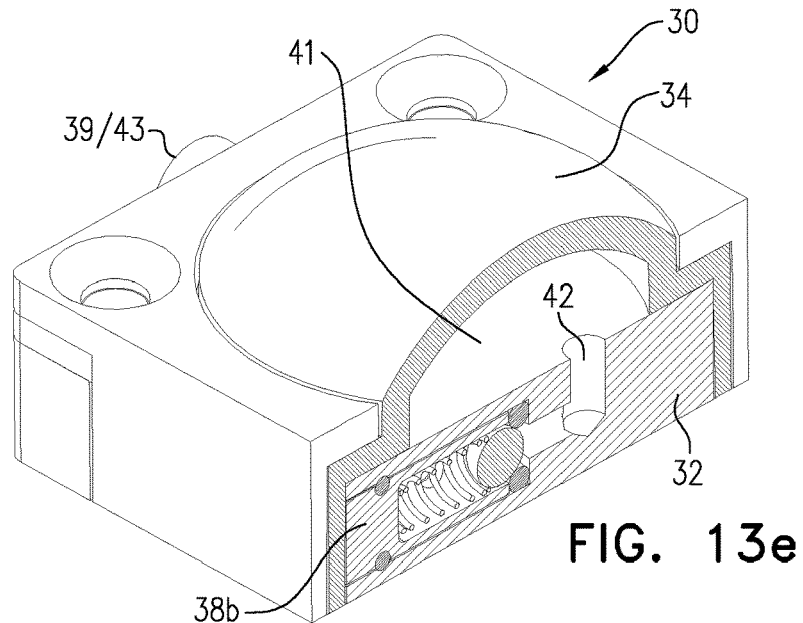

FIGS. 13*a*-13*e* provide additional views of the pump 30 from the example in FIGS. 11-12, as seen in a non-actuated state. FIG. 13*a* presents an isometric view of the pump 30; FIG. 13*b* provides a cross-sectional view of the pump 30, as seen along line b-b in FIG. 13*a*; FIG. 13*c* provides a cross-sectional view of the pump 30, as seen along line c-c in FIG. 13*a*; FIG. 13*d* provides a cross-sectional view of the pump 30, as seen along line d-d in FIG. 13*a*; and FIG. 13*e* provides a cross-sectional view of the pump 30, as seen along line e-e in FIG. 13*a*.

Figure 14A:
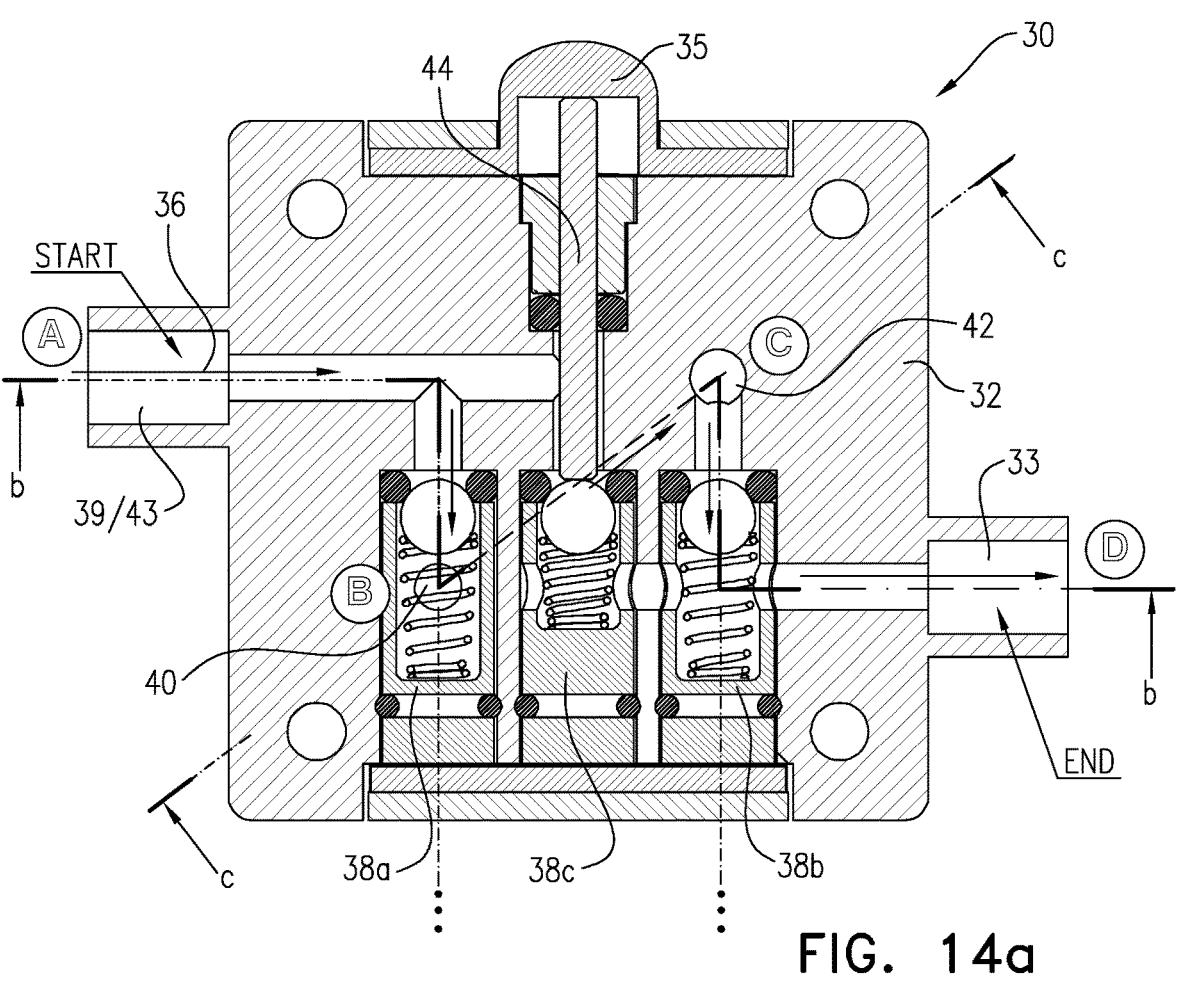
FIGS. 14*a*-14*c* show the pump in the blood flow regulator in FIG. 12, in an actuated state, as seen in several views, including: (a) a cross-section view as seen along line b-b in FIG. 13*a*; (b) a cross-section view as seen along line b-b in FIG. 14*a*; and (c) a cross-section view as seen along line c-c in FIG. 14*a;*
Figure 14B:
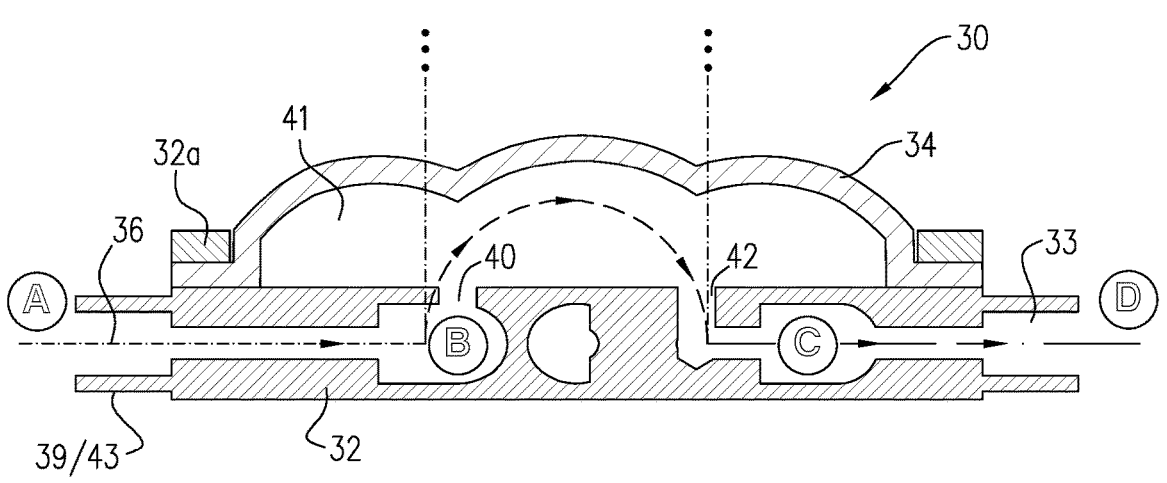
Figure 14C:
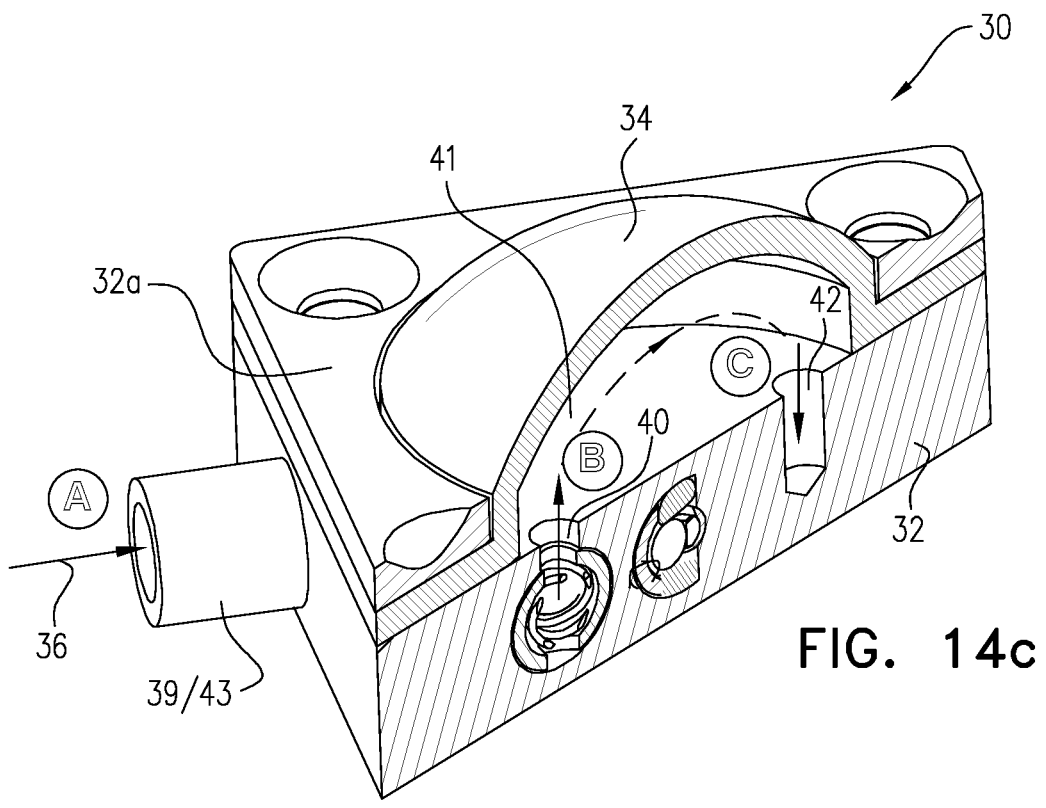
Figure 15A:
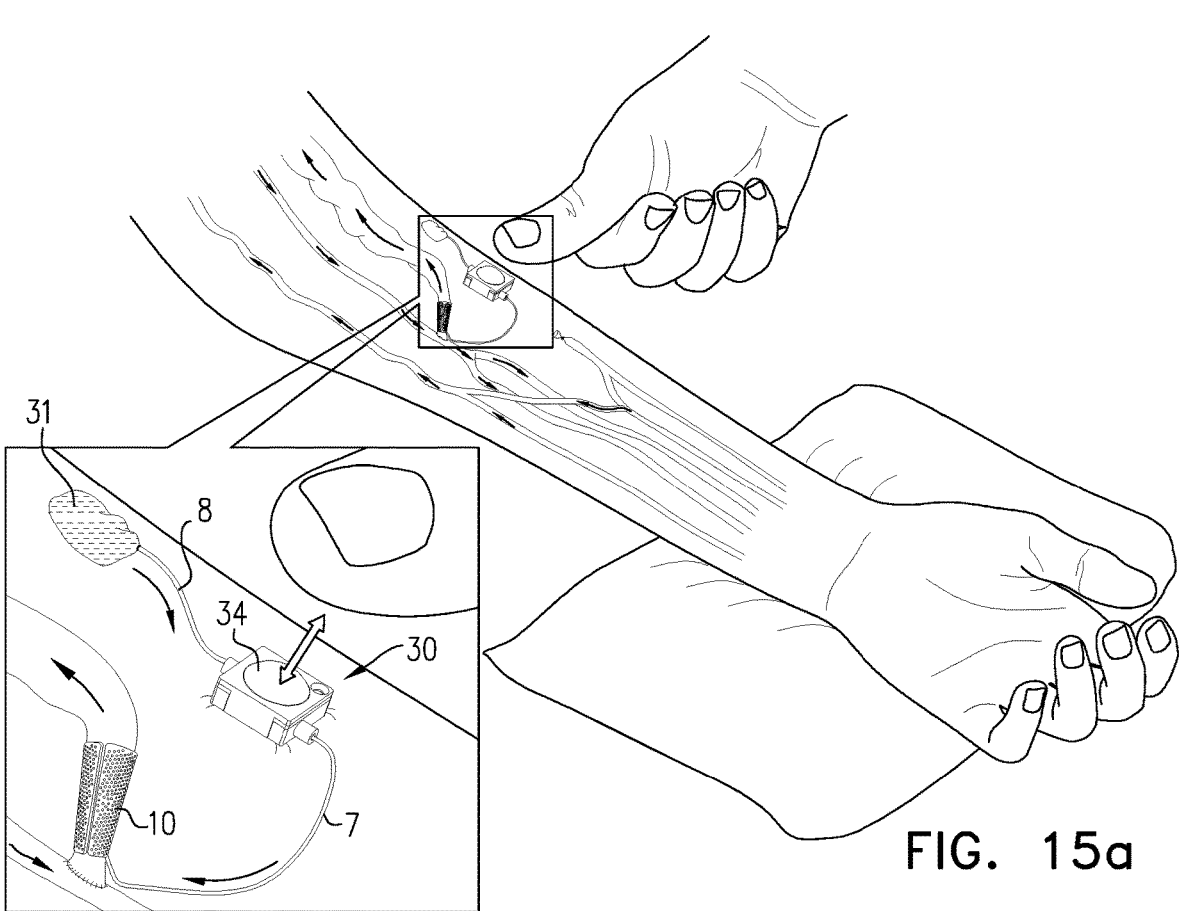
FIGS. 15*a*-15*b* illustrate a user operation of the blood flow regulator in accord with the actuated state in FIGS. 14*a*-14*c*, including (a) a user actuation of the pump for inflating an inflatable body at an implanted sheath of the device; and (b) a corresponding inflation of the inflatable body at the implanted sheath.
Figure 15B:
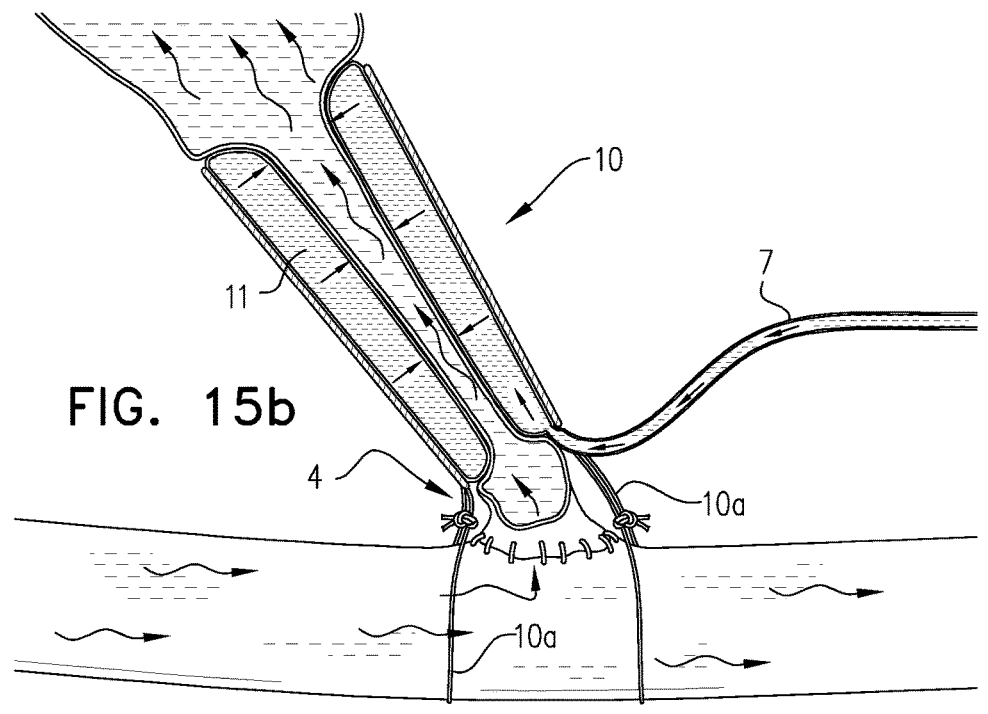

FIGS. 14*a*-14*c* shows the pump 30 from the example in FIGS. 11-12, as seen in an actuated state based on a compression of the elastic dome 34. FIG. 14*a* provides a top-down cross-sectional view as seen along line b-b of FIG. 13*a*, and FIG. 14*b* provides a cross-sectional view as seen along a line b-b in FIG. 14*a*, and FIG. 14*c* provides an isometric view of the cross-section seen along line c-c in FIG. 14*a*. In the actuated state shown in these figures, upon a compression of the elastic dome 34 (not shown), a quantity of fluid passes from the fluid reservoir 31 (not shown) into the fluid reservoir inlet 39, through the fluid circuit 32 via the dome inlet 40 and the dome outlet 42, and out the pump throat 33 for delivery to the inflatable body 11 of the sheath 10 via the fluid conduit 7. FIGS. 14*a*-14*c* provide a step-by-step illustration for the passage of fluid through the pump 30 during the actuated state shown in FIGS. 14*a*-14*c*. In particular, upon a compression of the elastic dome 34, a quantity of fluid passes from the fluid reservoir 31 into the fluid reservoir inlet 39, as seen at (A) in FIGS. 14*a*-14*c*. This fluid entering the pump 30 then passes into the first pressure valve 38*a* and through the dome inlet 40, as seen at (B) in FIGS. 14*a*-14*c*, to enter the dome inner space 41. The fluid traverses the dome inner space 41 and passes through the dome outlet 42, as seen at (C) in FIGS. 14*a*-14*c*, to enter the second pressure valve 38*b*. The fluid then travels to the pump throat 33 where it is then passed to the fluid conduit 7. A corresponding illustration of the actuation shown in FIGS. 14*a*-14*c* is provided in FIGS. 15*a*-15*b*, which show a user actuating the elastic dome 34 (FIG. 15*a*) with delivery of a fluid to the sheath 10 (FIG. 15*b*), which is fixed in place proximate to an AVF 4 via a fixing mechanism 10*a* (e.g., a pair of sutures), for inflation of the inflatable body 11. The fixing mechanism 10*a* is not limited to this example, and may be provided in other forms, including, for example, integrally formed clasping arms that wrap around a vascular lumen, as well as mating structures such as hooks and eyes, latches, straps, clips, or combinations thereof.

Figure 16:
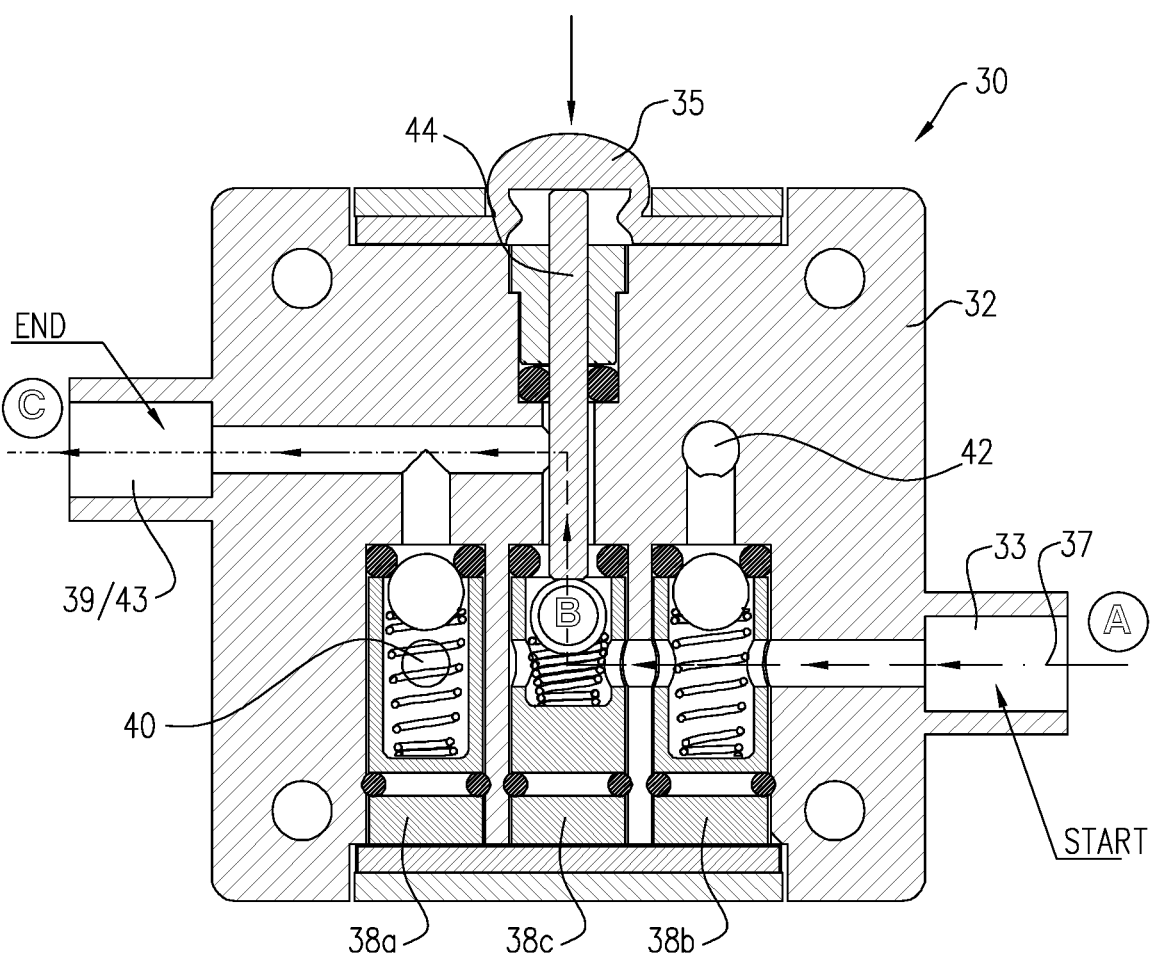
FIG. 16 shows the pump in the blood flow regulator in FIG. 12, in an actuated state, as seen in a cross-sectional view along line b-b in FIG. 13*a;*
Figures 17A, 17B:
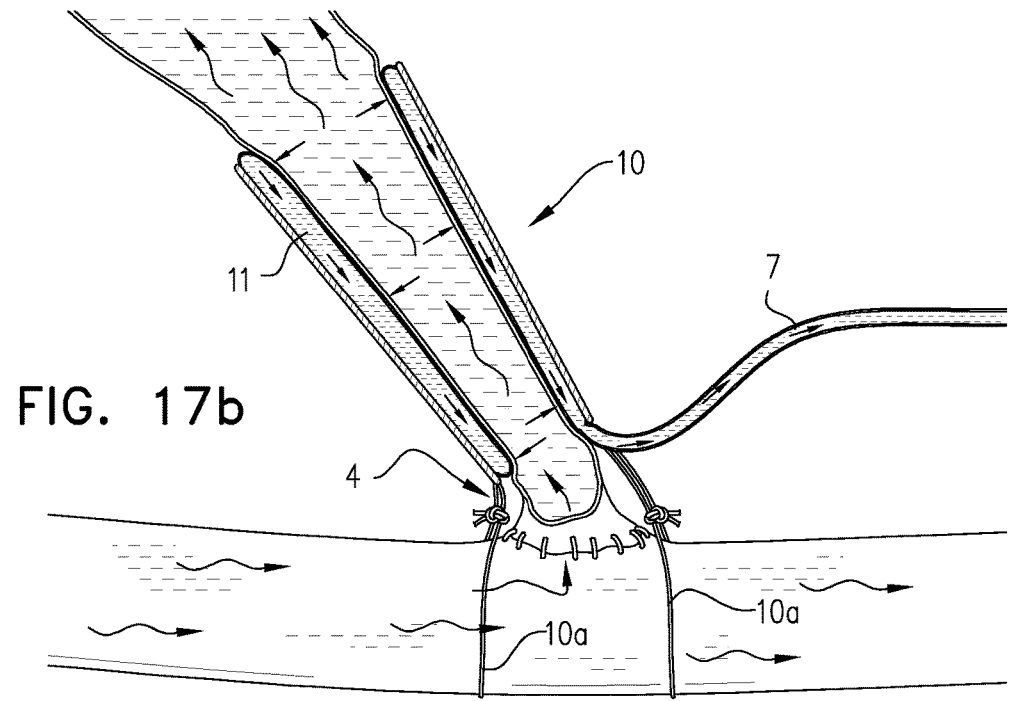
FIGS. 17*a*-17*b* illustrate a user operation of the blood flow regulator in accord with the actuated state in FIG. 16, including (a) a user actuation of the pump for deflating an inflatable body at an implanted sheath of the device; and (b) a corresponding deflation of the inflatable body at the implanted sheath.

FIG. 16 shows the pump 30 from the example in FIGS. 11-12, as seen in an actuated state based on a compression of the pressure button 35. FIG. 16 provides both a top-down cross-sectional view, as seen along line b-b of FIG. 13*a*. In this actuated state, upon a compression of the pressure button 35, the push rod 44 is caused to translate and compress the third pressure valve 38*c* to open the return path 37, thereby permitting a quantity of fluid to pass from the inflatable body 11 of the sheath 10, into the pump throat 33, through the fluid circuit 32 via the return path 37, and out the reservoir inlet 43 for delivery to the fluid reservoir 31 via the fluid conduit 8. FIG. 16 provides a step-by-step illustration for the passage of fluid through the pump 30 during the illustrated actuation state. In particular, upon a compression of the pressure button 35, the push rod 44 presses against a ball bearing to compress a biasing element in the third pressure valve 38*c*, thereby opening a fluid path through the third pressure valve 38*c*. At this time, a quantity of fluid passes from the inflatable body 11 of the sheath 10 to enter the pump 30 through the pump throat 33, as seen at (A) in FIG. 16. This fluid entering the pump 30 then bypasses the second pressure valve 38*b* to enter to third pressure valve 38*c* and pass through the fluid path formed therein, as seen at (B) in FIG. 16. The fluid then travels to the reservoir inlet 43 where it is then passed to the fluid conduit 8. A corresponding illustration of the actuation shown in FIG. 16 is provided in FIGS. 17*a*-17*b*, which show a user actuating the pressure button 35 (FIG. 17*a*) with withdrawal of a fluid from the sheath 10 (FIG. 17*b*), which is fixed in place proximate to an AVF 4 via a fixing mechanism 10*a* (e.g., a pair of sutures), for deflation of the inflatable body 11.

Figure 18A:
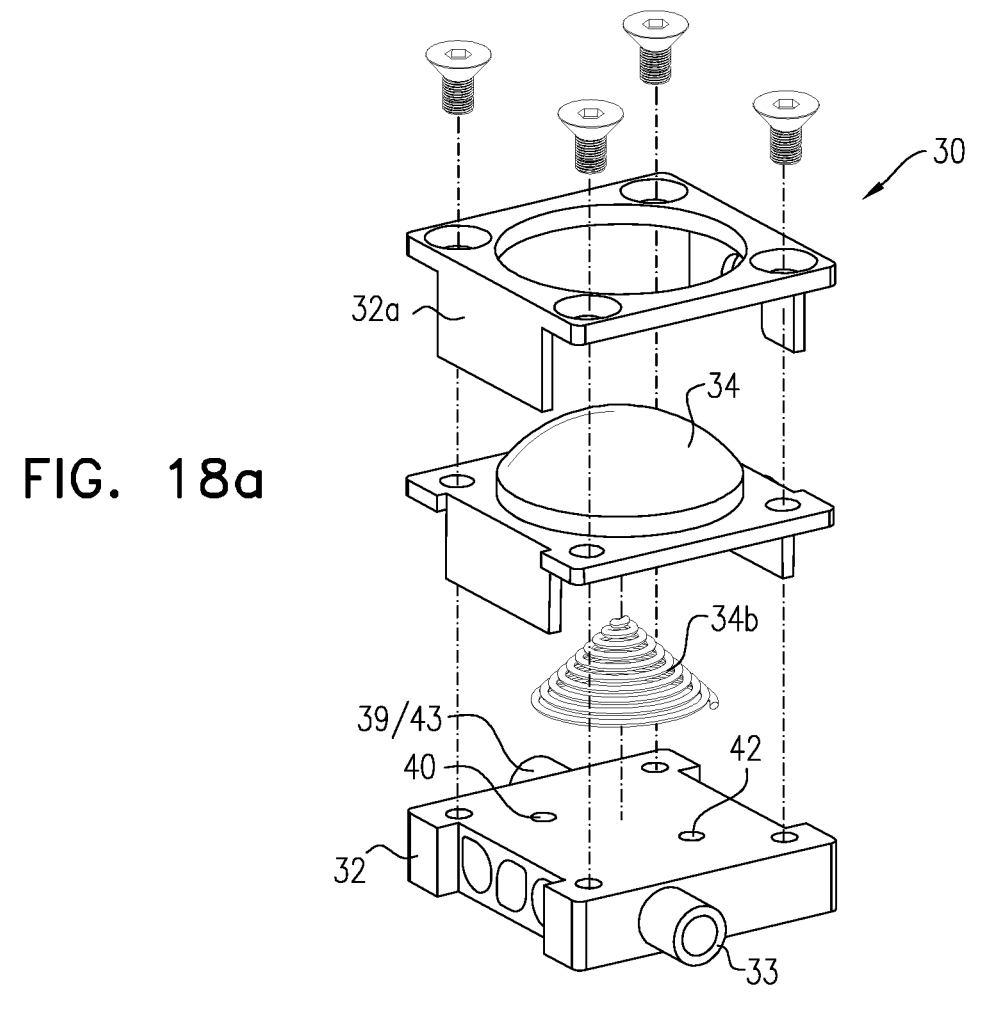
FIGS. 18*a*-18*b* show a construction of the pump in the blood flow regulator in FIG. 12 with an independent biasing element, including: (a) an exploded view of the pump; and (b) a cross-sectional view of the pump.
Figure 18B:
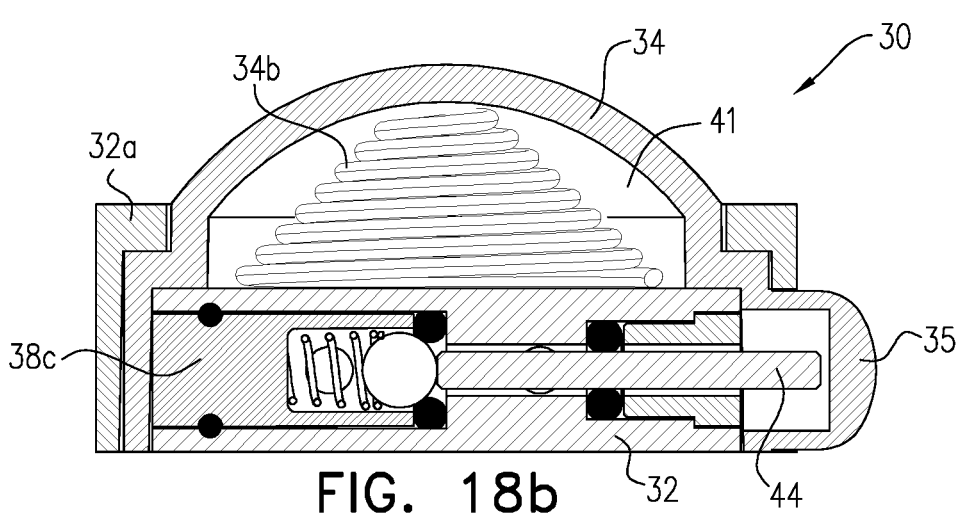

As discussed previously, the elastics dome 34 is an actuable surface that is available for manipulation by a user for effecting a pumping of fluid from the fluid reservoir 31, through the pump 30, and to the inflatable body 11 of the sheath 10. While it is contemplated that the elastic dome 34 will itself have an elastic biasing character that promotes a return of the dome 34 to an expanded state following a release of pressure by a user, the dome 34 may optionally house an additional independent biasing element 34*b* that further promotes a return of the dome 34 to an expanded state. FIGS. 18*a*-18*b* show one example of an independent biasing element 34*b* for inclusion within the dome 34 in the form of a spring 34*b*.

Figure 19:
FIG. 19 shows a construction of the pump in the blood flow regulator in FIG. 12 with a security mechanism, including views in an "on position" and an "off position"

As shown in FIG. 19, the pump 30 may optionally include a security mechanism 30*a* for preventing undesired, unintentional activation or deactivation of the pump 30. In this example, the pump 30 includes a switch that may be toggled between an "on position" that opens the fluid circuit 32 of the pump 30 and an "off position" that closes the fluid circuit 32. In the illustrated example, the security mechanism 30*a* is shown as a manual switch 30*a* that will reside below the skin and which a use may manually toggle between the "on" and "off" positions. The security mechanism 30*a* is not limited to this example, and may be provided in other forms, including, for example, a magnetic switch (e.g., a reed switch) that a user may toggle between the "on" and "off" positions via use of a magnetic or other device. With inclusion of a security mechanism 30*a*, a user may manipulate selectively activate or deactivate the pump 30, as a means for preventing unintentional activations of the pump 30 with inflation or deflation of the inflatable body 11.

Figure 21A:
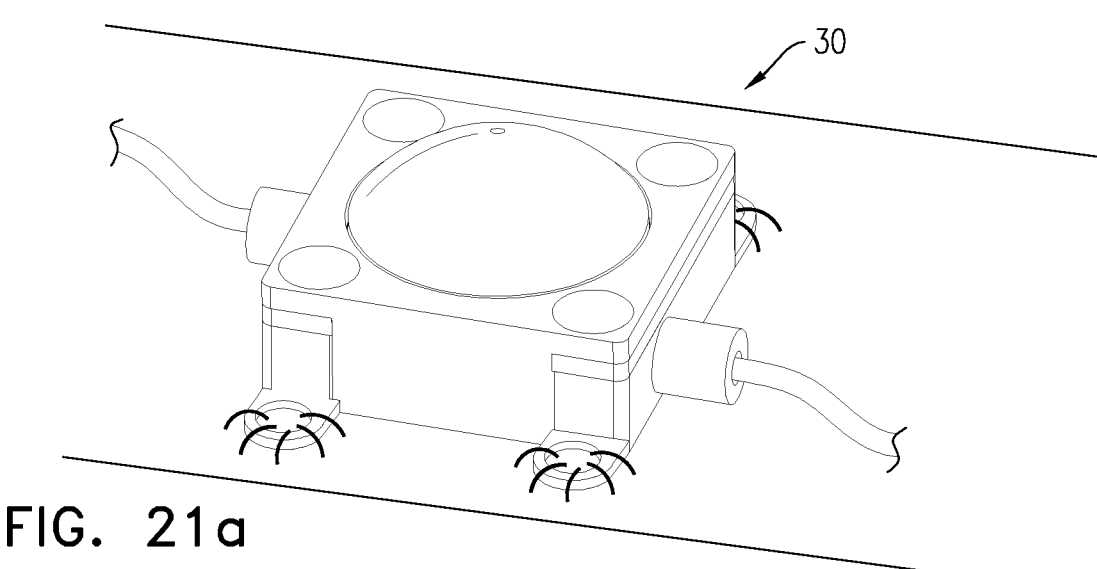
FIGS. 21*a*-21*b* show examples of a pump in the blood flow regulator in FIG. 12 fixed in place by, for example: (a) sutures; and (b) helical screws.
Figure 21B:
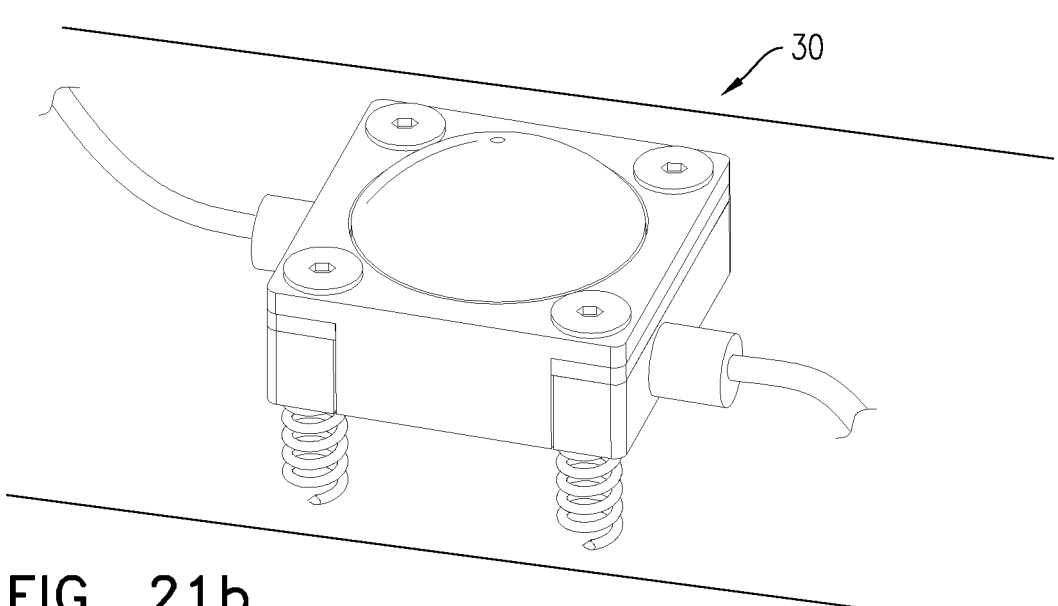

In use, a blood flow regulator 1 according to the present invention is implanted proximate to an AVJ. When used in connection with an AVF, the sheath 10 is positioned either on the artery, upstream of an anastomosis that joins the artery to a vein, or on the vein downstream of the anastomosis. When used in connection with an AVG, the sheath 10 may be placed on the artery, upstream of the anastomosis that joins the graft to the artery; on the vein, downstream of the anastomosis that joins the graft to the vein; or on the graft itself. In some examples, the sheath 10 may be formed integrally as a component of the graft in an AVG such that the sheath 10 is implanted concurrently upon implanting the graft to form the AVG. The pump 30 is implanted under the skin, subcutaneously at a sufficiently shallow depth, and at a convenient location for ease of user access to the actuable surfaces 34/35. The pump 30 may be mechanically secured in place, for example, by a number of surgical sutures, trocars, an adhesive, etc., as shown for example in FIGS. 21*a*-21*b*, with the implanted position depending on factors relevant to the specific patient, such as the patient's anatomy, body weight, former access, scars, etc. A length of the fluid conduit 7 may also be varied as needed to accommodate an implant position of the pump 30 relative to the sheath 10.

Figure 22:
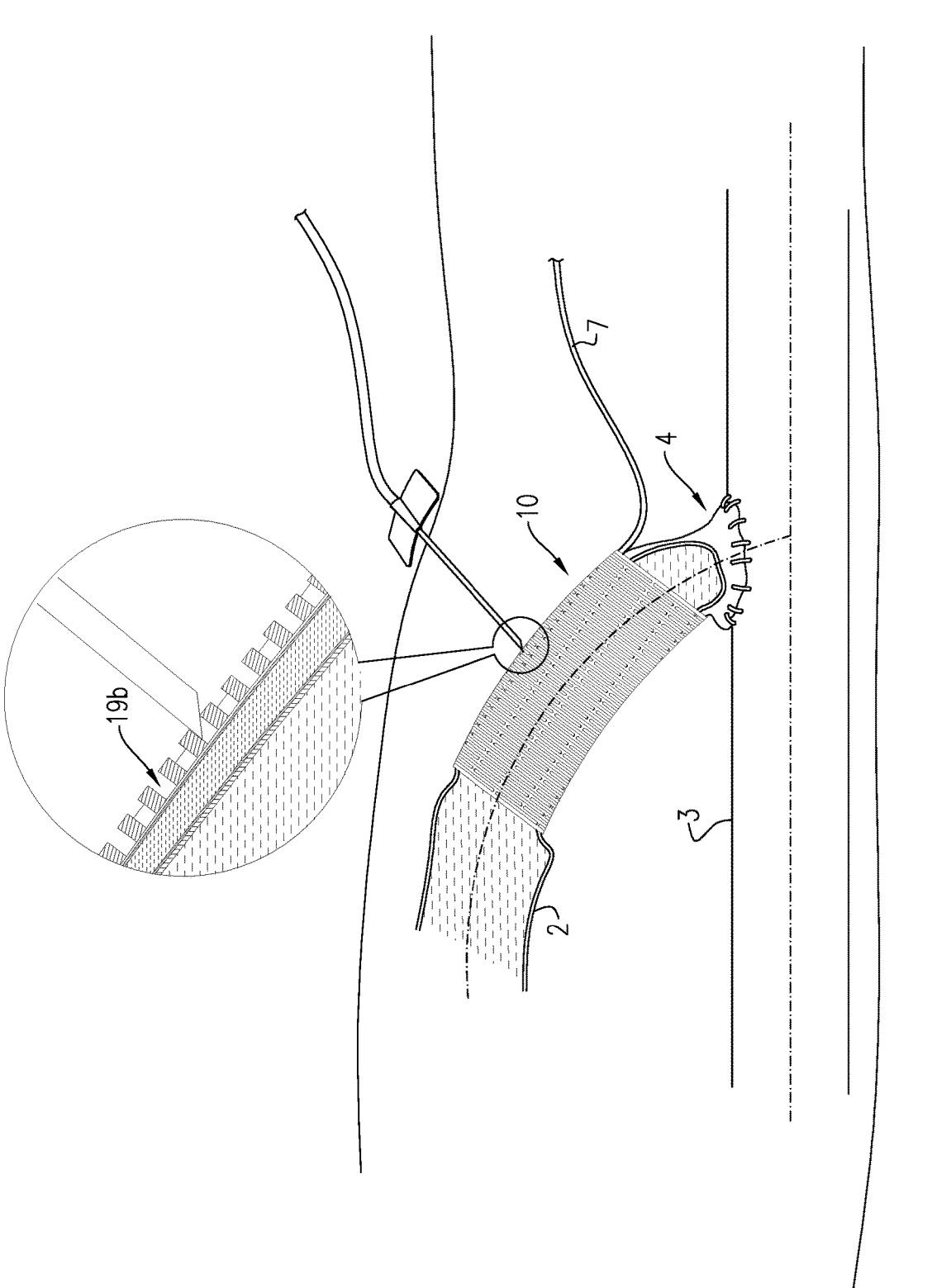
FIG. 22 shows an example of a blood flow regulator according to the present invention with a sheath that is made to be flexible for adapting to the shape of a vascular lumen, and provided with pores dimensioned to prevent piercing by a needle.

At the time of surgical implantation, the blood flow regulator 1 may be provided with the sheath 10 in the form of either a flattened sheet or a pre-curved sleeve. When provided in the form of a flattened sheet, the sheath 10 will have a relatively greater flexibility that permits the sheath 10 to be wrapped around a vascular lumen in a close-fitting shape that conforms to an outer circumference of the vascular lumen on which it is placed. In such examples, a physician may implant the sheath 10 by inserting a first end of the flattened sheet beside the vascular lumen and wrapping an opposite end of the sheet around the vascular lumen toward the first end of the sheet. When provided as a pre-curved sleeve, the sheath 10 may have a generally circular shape though with a space in the circumference thereof, between opposing opposite ends, so as to form a clamp with a C-shape. A clamp-type sheath 10 will have a relatively lesser flexibility with a degree of elasticity, as illustrated in FIG. 22, such that a slight pressure may be applied to slightly flex the sheath 10 to expand the spacing between the opposing opposite ends and permit insertion of a vascular vessel therethrough and within the curvature of the sheath 10, with the sheath 10 then rebounding slightly upon release of the pressure such that the spacing contracts and the sheath 10 clamps onto the vascular vessel. In both examples, a physician may insert the sheath 10 through manual manipulation of the sheath 10 alone and/or the physician may employ a tool for manipulating the sheath 10. Once the sheath 10 is positioned on a vascular lumen, a closure mechanism (if present) may be engaged to join first and second ends of the sheath 10 to one another (e.g., free ends of the flattened sheet; or free ends at the periphery of the spacing between opposing ends in the pre-curved sleeve).

Following sufficient maturation of a vascular lumen for use in hemodialysis treatment, an implanted blood flow regulator 1 may then be used to regulate a blood flow rate through the vascular lumen. When the patient is not receiving hemodialysis treatment, the blood flow regulator 1 may be controlled through the pump 30 to inflate the inflatable body 11 to compress the vascular lumen and restrict blood flow therethrough, thereby reducing a blood flow rate. When the patient is to receive hemodialysis treatment, the blood flow regulator 1 may be controlled through the pump 30 to deflate the inflated body 11 to permit the vascular lumen to expand thereby permitting an increased blood flow rate relative to the inflated state. Depending on the target blood flow rate prescribed for a specific patient's hemodialysis treatment, the inflatable body 11 may either be entirely deflated to remove all restriction to blood flow or may be only partially deflated to reduce a restriction to blood flow while still regulating blood flow to achieve a reduced blood flow rate relative to a natural unregulated blood flow rate. The degree to which the inflatable body 11 is deflated for hemodialysis treatment may vary from patient to patient, based on each patient's specific dialysis prescription and the natural blood flow rate of each patient in an unregulated state.

Figure 20:
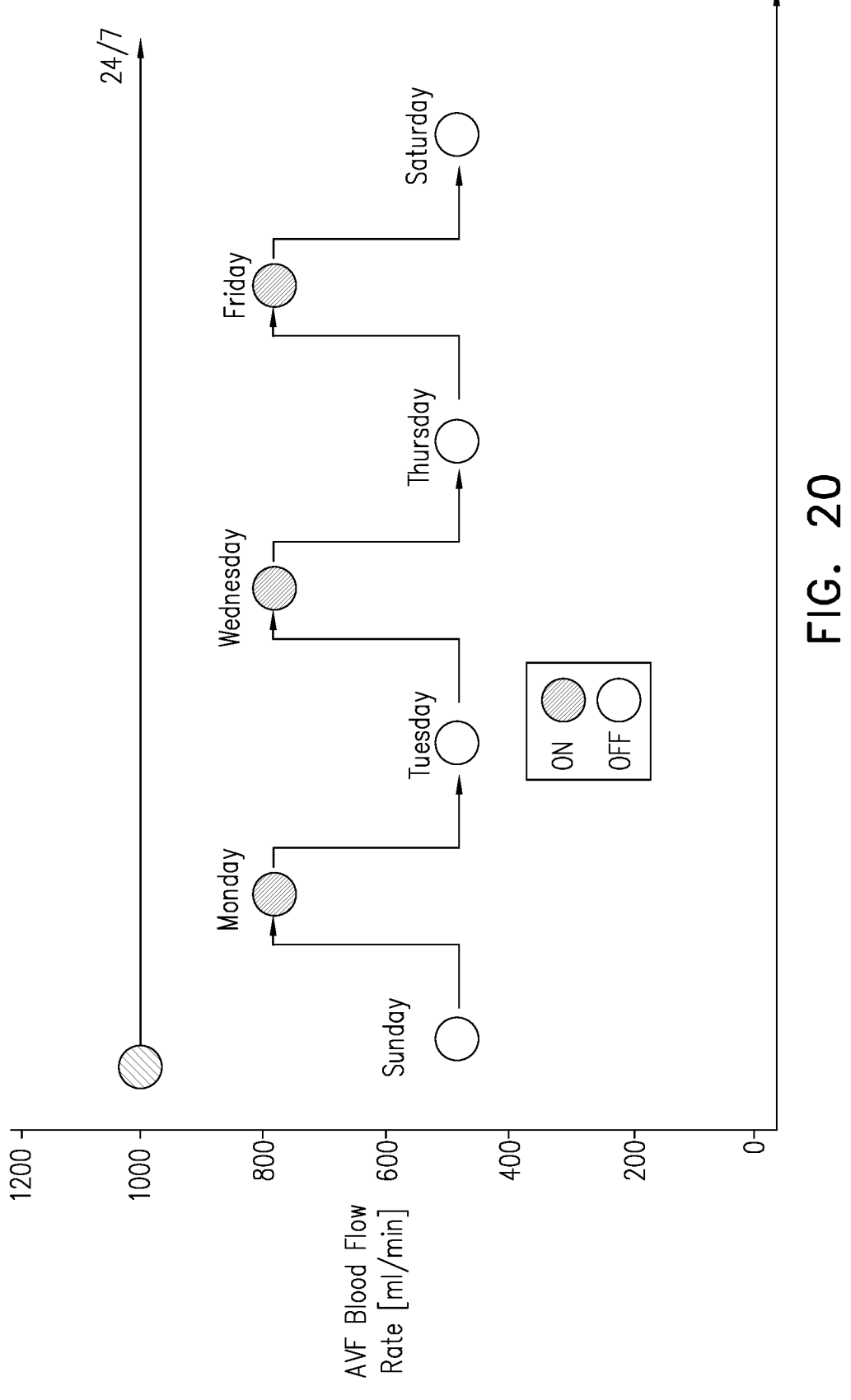
FIG. 20 shows an example of a hemodialysis treatment with the blood flow regulator in FIG. 3 as compared to a conventional hemodialysis treatment.

FIG. 20 shows one example of an inventive hemodialysis treatment according to the present invention, in which a blood flow regulator according to the present invention is used to regulate blood flow, as compared to a conventional hemodialysis treatment. In the conventional treatment a blood flow through the AVJ and the vascular lumen remains unregulated with the downstream vein being continuously subjected to the heightened blood pressure from the upstream arterial blood flow. Typically, a newly matured fistula results in a blood flow rate of at least 500 ml/min. However, as the fistula continues to mature, the vein diameter and blood flow rate will increase over time resulting in blood flow rates that are regularly above 1,000 ml/min, and potentially as high as approximately 2,000 ml/min in the absence of surgical intervention. Such elevated blood flow rates present a heightened risk of increased cardiac output and cardiac diseases; steal syndrome and/or ischemia; upper arm stenosis; and aneurysm formation. In the inventive treatment, a blood flow regulator according to the present invention is used to regulate blood flow through the AVJ and/or the vascular lumen to provide a requisite blood flow rate during on-treatment periods while reducing the blood flow rate during off-treatment periods. In the example shown in FIG. 20, during off-treatment days, the inflatable body 11 is inflated to reduce a diameter of the associated vascular lumen (e.g., a vein or graft), resulting in a reduced blood flow rate of approximately 500 ml/min; while during on-treatment days, the inflatable body 11 is deflated to permit expansion of the associated vascular lumen diameter, resulting in an increased blood flow rate of approximately 800 ml/min.

It will be understood, however, that methods according to the present invention are not limited to the example shown in FIG. 20, and that blood flow rates may vary based on a number of factors, including though not limited to the patient's anatomy, physiology, blood pressure, dialysis prescription, as well as the treating physician's advice. As such, in other examples, a blood flow rate during off-treatment days may be in a range from approximately 200 ml/min to approximately 600 ml/min, while a blood flow rate during on-treatment days may be in a range from approximately 300 ml/min to approximately 800 ml/min. It is noted that a blood flow rate during an on-treatment duration may be substantially similar to a blood flow rate during an off-treatment duration, as individual patients may experience different rates of fistula maturation as a result of the controlled treatment provided by a blood flow regulator according to the present invention. In particular, by adopting a blood flow regulator according to the present invention a patient may avoid a constantly elevated blood flow rate (e.g., over a 24/7 duration), and will instead be able to elevate their blood flow rate on demand, effectively permitting them to reduce the stresses incurred from an elevated blood flow rate to only those shortened durations when it is required for hemodialysis treatment (e.g., 4 hours on 3 days a week, for a total of 12 hours a week). Without being bound by theory, it is expected that such control of blood flow with a blood flow regulator according to the present invention may result in some patients experiencing significantly reduced fistula maturation over time, with the vein experiencing less stress and therefore incurring a lesser increase in maximum diameter, such that blood flows observed during off- and on-treatment periods are substantially similar. At the same time, it is expected that, even with the benefits of a blood flow regulator according to the present invention, some patients may still experience considerable fistula maturation over time, such that a blood flow rate observed during an on-treatment period is noticeably elevated relative to a blood flow observed during an off-treatment period.

Without being bound by theory, it is expected that blood flow regulators according to the present invention may achieve up to a 75% reduction in blood flow rates during on-treatment periods, as compared to blood flow rates that may be observed in conventional, unregulated treatments. For example, whereas conventional treatment without regulation of blood flow through the fistula may result in a heavily matured fistula having a blood flow rate of approximately 2,000 ml/min, methods performed according to the present invention with regulation of blood flow through the fistula may result in an on-treatment blood flow rate of approximately 500 ml/min.

As a heightened blood flow rate is required only during hemodialysis treatment itself, a blood flow regulator according to the present invention may be used to regulate the blood flow rate at lower rates during off-treatment periods while providing increased rates during on-treatment periods. Regulation of the blood flow rate may be adapted to the specific patient's conditions and dialysis prescription. In this way, the blood flow rate is regulated to provide a balanced flow rate that meets the requirements for hemodialysis treatment while also lessening the cardiovascular impact to the patient during off-treatment periods to thereby reduce risks associated with hemodialysis treatment.

Though the present invention is described with reference to particular embodiments, it will be understood to those skilled in the art that the foregoing disclosure addresses exemplary embodiments only; that the scope of the invention is not limited to the disclosed embodiments; and that the scope of the invention may encompass additional embodiments embracing various changes and modifications relative to the examples disclosed herein without departing from the scope of the invention as defined in the appended claims and equivalents thereto.

To the extent necessary to understand or complete the disclosure of the present invention, all publications, patents, and patent applications mentioned herein are expressly incorporated by reference herein to the same extent as though each were individually so incorporated.

The present invention is not limited to the exemplary embodiments illustrated herein, but is instead characterized by the appended claims, which in no way limit the scope of the disclosure.

What is claimed is:

1. A blood flow regulator for regulating a blood flow adjacent to an arteriovenous junction, the blood flow regulator comprising:

a vascular fitment adapted for implantation at a vascular lumen, the vascular fitment comprising an adjustable flow restrictor adapted for influencing a blood flow rate through the vascular lumen and a protective frame enclosing the flow restrictor; and a flow controller adapted to communicate with the flow restrictor for controlling adjustment of the flow restrictor, wherein the flow restrictor is adjustable between at least a first state for permitting a first blood flow rate through the vascular lumen and a second state for permitting a second blood flow rate through the vascular lumen, the first and second blood flow rates differing from one another, and the protective frame comprises a plurality of pores formed therein, the plurality of pores comprising pores of varying sizes in which relatively larger pores are provided at a first end of the protective frame and relatively smaller pores are provided at a second end of the protective frame.

2. The blood flow regulator according to claim 1, wherein the vascular fitment further comprises a coating provided between the flow restrictor and the protective frame, the coating being formed of a material that promotes adhesion between the flow restrictor and the protective frame.

3. The blood flow regulator according to claim 2, wherein the coating is applied to encapsulate the protective frame with the coating distributed through the plurality of pores.

4. The blood flow regulator according to claim 2, wherein the coating is applied only on an interior surface of the protective frame.

5. The blood flow regulator according to claim 3, wherein the protective frame is made of at least one material selected from: polyethylene terephthalate (PET), polytetrafluoroethylene (ePTFE), nylon, polypropylene, thermoplastic polyurethane (TPU), Polyether ether ketone (PEEK), cobalt chromium, and Nitinol.

6. The blood flow regulator according to claim 3, wherein the coating is made of at least one material selected from: a thermoplastic elastomer (TPE) and a thermoset elastomer (TSE).

7. The coating according to claim 6, wherein the coating is made of a thermoplastic polyurethane (TPU).

8. The blood flow regulator according to claim 1, wherein the plurality of pores are dimensioned to resist the passage of a cannulation needle and thereby protect against damage to the flow restrictor.

9. The blood flow regulator according to claim 1, wherein the size of the pores gradually decreases from the relatively larger pores at the first end to the relatively smaller pores at the second end.

10. The blood flow regulator according to claim 1, wherein the flow restrictor is adjustable between a first state having a first volume and a second state having a second volume, the second volume being greater than the first volume, and the flow restrictor is adapted such that changes between the first volume and the second volume occur substantially uniformly throughout the flow restrictor.

11. The blood flow regulator according to claim 10, wherein the flow restrictor comprises an inflatable body adapted for adjustment between a the first state being a deflated state having the first volume and the second state being an inflated state having the second volume, and the inflatable body comprises a perimeter that defines an interior space for reception of a fluid flow for inflating the inflatable body, and a number of flow barriers within the interior space for guiding a fluid flow for promoting a substantially uniform distribution of a fluid flow within the interior space.

12. The blood flow regulator according to claim 11, wherein the vascular fitment further comprises a coating provided between the protective frame and the inflatable body, the coating having the same mechano-chemical properties as the inflatable body.

13. The blood flow regulator according to claim 12, wherein the coating is the made of the same material as the inflatable body.

14. The blood flow regulator according to claim 11, wherein the inflatable body is made of at least one material selected from: a thermoplastic elastomer (TPE) and a thermoset elastomer (TSE).

15. The blood flow regulator according to claim 11, wherein
   at least one inner surface of the inflatable body has a roughened texture that prevents interior inner surfaces of the inflatable body from adhering to one another.

16. The blood flow regulator according to claim 15, wherein
   an outer surface of the inflatable body has a smoothened texture for reducing friction between the inflatable body and a vascular lumen upon inflation and deflation of the inflatable body.

17. The blood flow regulator according to claim 11, wherein
   the flow barriers are heat-fused, ultrasonic, or radio-frequency welds between opposing surfaces of the inflatable body.

18. The blood flow regulator according to claim 11, wherein
   a plurality of the number of flow barriers aligned along a length of the inflatable body separate the interior space into multiple regions of equal volume and define multiple fluid flow channels that promote uniform distribution of a fluid flow between an inlet to the interior space and the separate regions.

19. The blood flow regulator according to claim 11, wherein
   the vascular fitment is adapted for implantation around an outer circumference of a vascular lumen such that inflation of the inflatable body constricts a diameter of the vascular lumen to achieve a relatively lower blood flow rate and deflation of the inflatable body permits distension of a diameter of the vascular lumen to achieve a relatively higher blood flow rate.

20. The blood flow regulator according to claim 11, wherein
   the vascular fitment comprises a fixation mechanism for fixing the vascular fitment in place proximate to an arteriovenous junction.

21. The blood flow regulator according to claim 19, wherein
   the inflatable body comprises an exhaust valve that limits inflation of the inflatable body to a predetermined threshold.

22. The blood flow regulator according to claim 21, wherein
   the exhaust valve comprises at least one one-way elastic leaf valve that opens to provide a fluid flow path between the interior space of the inflatable body and an outside of the inflatable body.

23. The blood flow regulator according to claim 21, wherein
   the exhaust valve is adapted to provide a fluid flow path between the interior space of the inflatable body and a collection chamber.

24. The blood flow regulator according to claim 23, wherein
   the collection chamber is formed from a diffusible material that enables the diffusion of small molecules from an interior of the collection chamber to an exterior of the collection chamber.

25. The blood flow regulator according to claim 19, wherein
   the protective frame surrounds an outer periphery of the inflatable body to bias inflation of the inflatable body in a radially inward direction for applying pressure against an outer circumference of a vascular lumen.

26. The blood flow regulator according to claim 25, wherein
   the protective frame and the inflatable body share a common geometrical shape.

27. The blood flow regulator according to claim 26, wherein
   the common geometrical shape of the protective frame and the inflatable body is a cylindrical shape or a conical shape.

28. The blood flow regulator according to claim 25, wherein
   the protective frame is made sufficiently flexible such that the protective frame adapts to the shape and geometry of the vascular lumen.

29. The blood flow regulator according to claim 25, wherein
   the protective frame comprises a closure mechanism for joining first and second ends of the protective frame to one another, and further preventing biased inflation of the inflatable body in an outward direction.

30. The blood flow regulator according to claim 29, wherein
   the closure mechanism comprises at least one of: hooks, eyes, zip locks, latches, straps, clips, or combinations thereof.

31. The blood flow regulator according to claim 11, wherein
   the flow controller comprises a fluid reservoir and a fluid conduit for communicating a fluid flow between the fluid reservoir and the vascular fitment for adjusting the inflatable body between the first deflated state and the second inflated state.

32. The blood flow regulator according to claim 31, wherein
   the flow controller further comprises a fluid circuit between the fluid reservoir and the fluid conduit, the fluid circuit having a discharging path for discharging a fluid flow from the fluid reservoir to the inflatable body via the fluid conduit and a return path for returning a fluid from the inflatable body to the fluid reservoir via the fluid conduit.

33. The blood flow regulator according to claim 32, wherein
   the flow controller comprises a pump housing the fluid circuit, and the fluid reservoir is integrated with the pump.

34. The blood flow regulator according to claim 32, wherein
   the flow controller comprises a pump housing the fluid circuit, and the fluid reservoir is independent from the pump with a second fluid conduit provided for communicating a fluid flow between the fluid reservoir and the pump.

35. The blood flow regulator according to claim 31, wherein
   the discharge path is configured to discharge multiple fluid flows from the fluid reservoir to the inflatable body in discrete volumes over multiple activations of an actuable-surface, and the return path is configured to return substantially all fluid stored in the inflatable body to the fluid reservoir in a single activation of an actuable-surface.

36. The blood flow regulator according to claim 35, wherein the discharge path is configured to discharge fluid upon actuation of a first actuable-surface and the return path is configured to return fluid upon actuation of a second, different actuable-surface.

37. The blood flow regulator according to claim 36, wherein the first actuable-surface is a compressible elastic dome having an interior space for reception of a volume of fluid, the elastic dome being configured such that, upon application of a pressure thereto, the elastic dome compresses to force a first volume of fluid contained within the interior space through the fluid conduit for delivery to the inflatable body, and upon release of the pressure thereto, the elastic dome rebounds to a non-compressed state and creates a vacuum force that draws a second volume from the fluid reservoir and into the fluid circuit for reception in the interior space.

38. The blood flow regulator according to claim 37, wherein the interior space of the elastic dome is provided with a defined volume such that each application and release of a pressure to the elastic dome results in a substantially identical volume of fluid being drawn into the interior space of the elastic dome.

39. The blood flow regulator according to claim 37, wherein the fluid circuit is configured to provide a one-way flow of fluid upon actuation.

40. The blood flow regulator according to claim 39, wherein the fluid circuit comprises a first pressure valve that restricts a flow of fluid into the interior space of the elastic dome, and a second pressure valve that restricts a flow of fluid out from the interior space of the elastic dome, the first and second pressure valves are configured such that upon compression of the elastic dome, an increased pressure applied on a first volume of fluid contained within the interior space of the elastic dome causes the second pressure valve to open for receiving the first volume of fluid, while the first pressure valve remains closed, and upon rebound of the elastic dome, an increased vacuum force within the interior space of the elastic dome causes the first pressure valve to open for delivering a second volume of fluid for reception within the interior space of the elastic dome, while the second pressure valve closes.

41. The blood flow regulator according to claim 36, wherein the second actuable-surface is a pressure button that opens the return path to bypass a flow restriction controlled by the first actuable-surface.

42. The blood flow regulator according to claim 41, wherein the pressure button is configured, upon application of a pressure thereto, to drive a push rod to force open a pressure valve for opening the return path, and upon release of the pressure thereto, to permit withdrawal of the push rod and closure of the pressure valve.

43. The blood flow regulator according to claim 36, wherein the actuable-surfaces may be any combination of mechanically, electrically, pneumatically, and hydraulically actuable surfaces.

44. The blood flow regulator according to claim 31, wherein the fluid reservoir comprises an embedded port that is adapted to provide a fluid path for refilling the fluid reservoir.

45. The blood flow regulator according to claim 44, wherein the embedded port is adapted for access by a surgical needle for refilling the fluid reservoir subsequent to implantation of the blood flow regulator.

46. The blood flow regulator according to claim 32, wherein the flow controller further comprises at least one valve for controlling a fluid flow through the fluid circuit and a security mechanism adapted to prevent unattended activation of the blood flow regulator by blocking a fluid flow through the at least one valve.

47. The blood flow regulator according to claim 46, wherein the security mechanism is adapted for mechanical and/or magnetic activation for enabling the at last one valve to permit a fluid flow through the fluid circuit between the fluid reservoir and the inflatable body.

48. The blood flow regulator according to claim 31, wherein the inflatable body is adapted to receive a fluid flow from the fluid reservoir, in the form of a liquid flow, that fills and inflates the inflatable body against an outer wall of a vascular lumen.

49. The blood flow regulator according to claim 48, wherein the liquid flow comprises at least one of: medical grade saline, water, oil, glycerol, or a combination thereof.

50. The blood flow regulator according to claim 48, wherein the inflatable body comprises multiple layers.

51. The blood flow regulator according to claim 48, wherein the inflatable body comprises a protective layer that resists diffusion of the liquid flow through the inflatable body.

52. The blood flow regulator according to claim 51, wherein the protective layer comprises a material that mitigates the passage of liquid molecules through pores in the inflatable body.

53. A method of making a blood flow regulator according to claim 2, comprising applying a coating material to the protective frame in a liquid state, and hardening the coating material to a solid state to form the coating.

54. The method according to claim 53, wherein the coating material is applied by one of: brushing, dip-coating, spraying, or spin coating.

55. A method of configuring a vascular lumen comprising:

implanting a blood flow regulator according to claim 1 with the vascular fitment positioned at a vascular lumen.

56. The method according to claim 55, wherein the vascular lumen is a vein, and the vascular fitment is positioned at a downstream position of the vein, in a blood flow direction, from an anastomosis that provides a blood flow connection between the vein and an artery.

57. The method according to claim 55, wherein the vascular lumen is an artery, and the vascular fitment is positioned at an upstream position of the artery, in a blood flow direction, from an anastomosis that provides a blood flow connection between the artery and a vein.

58. The method according to claim 55, wherein the vascular lumen is a graft in an arteriovenous graft that joins and provides a blood flow between an artery and a vein, and the vascular fitment is positioned at the graft between the artery and the vein.

59. The method according to claim 55, wherein the vascular fitment is positioned on the vascular lumen proximate to an anastomosis that provides a blood flow connection between an artery and a vein, with the vascular fitment oriented on the vascular lumen such that the first end of the protective frame is closer to the anastomosis and the second end of the protective frame is further from the anastomosis.

60. The method according to claim 55, wherein the blood flow regulator is secured under the skin, in the subcutaneous region.

61. A method for controlling blood flow through a vascular lumen comprising:
utilizing a blood flow regulator according to claim 1 with the vascular fitment positioned at a vascular lumen.

62. The method according to claim 61, further comprising:
actuating the fluid controller to adjust the flow restrictor between the first state that yields a relatively increased blood flow rate and the second state that yields a relatively decreased blood flow rate.

63. The method according to claim 62, wherein:
the flow restrictor comprises an inflatable body adapted for adjustment between the first state corresponding with a deflated state and the second state corresponding with an inflated state, and
actuating the fluid controller comprises at least one of:
actuating a fluid circuit to discharge a fluid flow from a fluid reservoir to the inflatable body for inflating the inflatable body to constrict the vascular lumen for reducing a blood flow rate, and
actuating a fluid circuit to return a fluid flow from the inflatable body to a fluid reservoir for deflating the inflatable body to distend the vascular lumen for increasing a blood flow rate.

64. The method according to claim 63, wherein
actuating the fluid circuit to discharge a fluid flow from the fluid reservoir to the inflatable body for inflating the inflatable body comprises multiple actuations for discharging multiple discrete fluid flows from the fluid reservoir to the inflatable body in discrete volumes for incremental inflation of the inflatable body, and
actuating the fluid circuit to return a fluid flow from the inflatable body to the fluid reservoir comprises a single actuation for returning substantially all fluid stored in the inflatable body to the fluid reservoir.

* * * * *